(12) United States Patent
Hershey et al.

(10) Patent No.: US 9,849,287 B2
(45) Date of Patent: Dec. 26, 2017

(54) SYSTEM AND METHOD FOR DETERMINING THE NEUROLOGICAL POSITION OF EPIDURAL LEADS

(71) Applicant: Boston Scientific Neuromodulation Corporation, Valencia, CA (US)

(72) Inventors: Bradley Lawrence Hershey, Valencia, CA (US); Michael A. Moffitt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 3 days.

(21) Appl. No.: 15/017,906

(22) Filed: Feb. 8, 2016

(65) Prior Publication Data

US 2016/0228706 A1    Aug. 11, 2016

Related U.S. Application Data

(60) Provisional application No. 62/113,654, filed on Feb. 9, 2015.

(51) Int. Cl.
*A61N 1/36* (2006.01)
*A61N 1/05* (2006.01)
*A61N 1/372* (2006.01)

(52) U.S. Cl.
CPC ....... *A61N 1/36071* (2013.01); *A61N 1/0551* (2013.01); *A61N 1/36132* (2013.01);
(Continued)

(58) Field of Classification Search
CPC .............. A61N 1/36071; A61N 1/0551; A61N 1/36132
See application file for complete search history.

(56) References Cited

U.S. PATENT DOCUMENTS 5,938,690 A    8/1999  Law et al.
5,941,906 A    8/1999  Barreras, Sr. et al.
(Continued)

FOREIGN PATENT DOCUMENTS

WO    WO-2006029257 A2    3/2006
WO    WO-2006135791 A2    12/2006
(Continued)

OTHER PUBLICATIONS

Barolat, Giancarlo, et al., "Mapping of sensory responses to epidural stimulation of the intraspinal neural structures in man", J. Neurosurg, vol. 78, Feb. 1993, 233-239.
(Continued)

*Primary Examiner* — Joseph Dietrich
(74) *Attorney, Agent, or Firm* — Schwegman Lundberg & Woessner, P.A.

(57) ABSTRACT

An system may include an electrode arrangement configured for implantation in an epidural space, a neural modulation generator configured to use electrodes in the electrode arrangement to generate modulation fields, at least one storage and a controller operably connected to the neural modulation generator. The storage(s) may be configured to store supra-perception threshold dorsal root modulation field parameter data and therapeutic modulation field parameter data, where the therapeutic modulation field parameter data may be different than the supra-perception threshold dorsal root modulation field parameter data. The system may be configured to deliver a placement modulation field from the electrode arrangement in the epidural space to the dorsal roots using the supra-perception threshold dorsal root modulation field parameter data, and deliver a therapeutic modulation field from the electrode arrangement placed in the desired position within the epidural space to a therapeutic
(Continued)

neural target using the therapeutic modulation field parameter data.

20 Claims, 15 Drawing Sheets

(52) U.S. Cl.
    CPC ..... *A61N 1/37241* (2013.01); *A61N 1/37247* (2013.01); *A61N 1/36185* (2013.01)

(56) References Cited

U.S. PATENT DOCUMENTS

| | | | |
|---|---|---|---|
| 6,516,227 | B1 | 2/2003 | Meadows et al. |
| 6,675,046 | B2 | 1/2004 | Holsheimer |
| 6,895,280 | B2 | 5/2005 | Meadows et al. |
| 6,993,384 | B2 | 1/2006 | Bradley et al. |
| 7,317,948 | B1 | 1/2008 | King et al. |
| 7,333,857 | B2 | 2/2008 | Campbell |
| 7,539,538 | B2 | 5/2009 | Parramon et al. |
| 7,650,184 | B2 | 1/2010 | Walter |
| 7,979,133 | B2 | 7/2011 | Feler et al. |
| 7,987,000 | B2 | 7/2011 | Moffitt et al. |
| 8,019,439 | B2 | 9/2011 | Kuzma et al. |
| 8,160,328 | B2 | 4/2012 | Goetz et al. |
| 8,180,129 | B2 | 5/2012 | Goetz et al. |
| 8,224,453 | B2 | 7/2012 | De Ridder |
| 8,255,057 | B2 | 8/2012 | Fang et al. |
| 8,355,797 | B2 | 1/2013 | Caparso et al. |
| 8,412,345 | B2 | 4/2013 | Moffitt |
| 8,437,857 | B2 | 5/2013 | Moffitt et al. |
| 8,455,716 | B2 | 6/2013 | Huang et al. |
| 8,504,147 | B2 | 8/2013 | Deem et al. |
| 8,615,300 | B2 | 12/2013 | Feler et al. |
| 8,649,874 | B2 | 2/2014 | Alataris et al. |
| 8,660,653 | B2 | 2/2014 | Kothandaraman |
| 8,670,831 | B2 | 3/2014 | Wacnik et al. |
| 8,676,329 | B2 | 3/2014 | Wacnik et al. |
| 8,676,331 | B2 | 3/2014 | Parker |
| 8,700,178 | B2 | 4/2014 | Anderson |
| 8,731,675 | B2 | 5/2014 | Ranu et al. |
| 8,751,009 | B2 | 6/2014 | Wacnik |
| 9,192,760 | B2 | 11/2015 | Bradley et al. |
| 2003/0139781 | A1 | 7/2003 | Bradley et al. |
| 2004/0116978 | A1 | 6/2004 | Bradley |
| 2007/0021801 | A1 | 1/2007 | Heruth et al. |
| 2007/0150036 | A1 | 6/2007 | Anderson |
| 2007/0203538 | A1 | 8/2007 | Stone et al. |
| 2008/0188909 | A1 | 8/2008 | Bradley |
| 2009/0196472 | A1 | 8/2009 | Goetz et al. |
| 2009/0198306 | A1 | 8/2009 | Goetz et al. |
| 2009/0204173 | A1 | 8/2009 | Fang et al. |
| 2010/0010566 | A1 | 1/2010 | Thacker et al. |
| 2010/0023090 | A1 | 1/2010 | Jaax et al. |
| 2010/0121409 | A1 | 5/2010 | Kothandaraman et al. |
| 2010/0274312 | A1 | 10/2010 | Alataris et al. |
| 2010/0274314 | A1 | 10/2010 | Alataris et al. |
| 2010/0274315 | A1 | 10/2010 | Alataris et al. |
| 2010/0274317 | A1 | 10/2010 | Parker et al. |
| 2010/0274318 | A1 | 10/2010 | Walker et al. |
| 2010/0274326 | A1 | 10/2010 | Chitre et al. |
| 2011/0093047 | A1 | 4/2011 | Davis et al. |
| 2011/0282414 | A1 | 11/2011 | Kothandaraman et al. |
| 2012/0059446 | A1 | 3/2012 | Wallace et al. |
| 2012/0083709 | A1 | 4/2012 | Parker et al. |
| 2012/0083857 | A1 | 4/2012 | Bradley |
| 2012/0101537 | A1 | 4/2012 | Peterson et al. |
| 2012/0158096 | A1 | 6/2012 | Sherman |
| 2012/0253422 | A1 | 10/2012 | Thacker et al. |
| 2012/0265279 | A1 | 10/2012 | Zhu et al. |
| 2012/0283797 | A1 | 11/2012 | De Ridder |
| 2012/0290041 | A1 | 11/2012 | Kim et al. |
| 2013/0066411 | A1 | 3/2013 | Thacker et al. |
| 2013/0116752 | A1 | 5/2013 | Parker et al. |
| 2013/0158628 | A1 | 6/2013 | Kothandaraman |
| 2013/0268021 | A1 | 10/2013 | Moffitt |
| 2013/0296975 | A1 | 11/2013 | Lee et al. |
| 2014/0081349 | A1 | 3/2014 | Lee et al. |
| 2014/0277267 | A1 | 9/2014 | Vansickle et al. |
| 2014/0371819 | A1 | 12/2014 | Goetz et al. |
| 2015/0119958 | A1 | 4/2015 | Li et al. |

FOREIGN PATENT DOCUMENTS

| | | |
|---|---|---|
| WO | WO-2009097224 A1 | 8/2009 |
| WO | WO-2010045481 A2 | 4/2010 |
| WO | WO-2015066295 A1 | 5/2015 |
| WO | WO-2016130454 A1 | 8/2016 |

OTHER PUBLICATIONS

"International Application Serial No. PCT/US2016/016936, International Search Report dated May 10, 2016", 4 pgs.
"International Application Serial No. PCT/US2016/016936, Written Opinion dated May 10, 2016", 6 pgs.

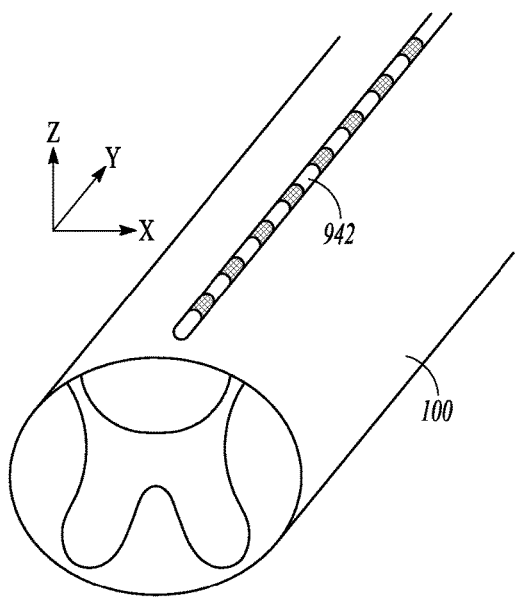
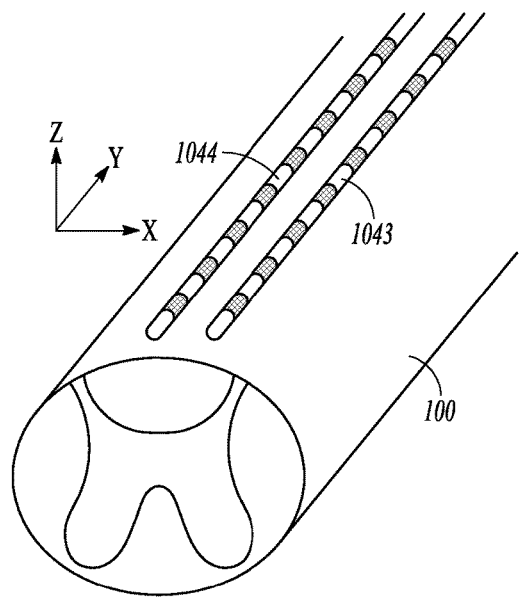
FIG. 9  FIG. 10
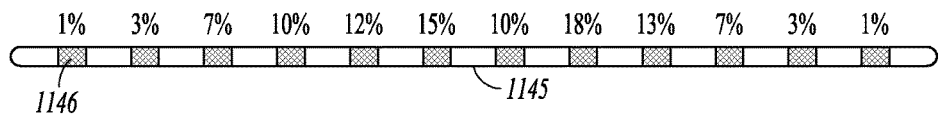
FIG. 11

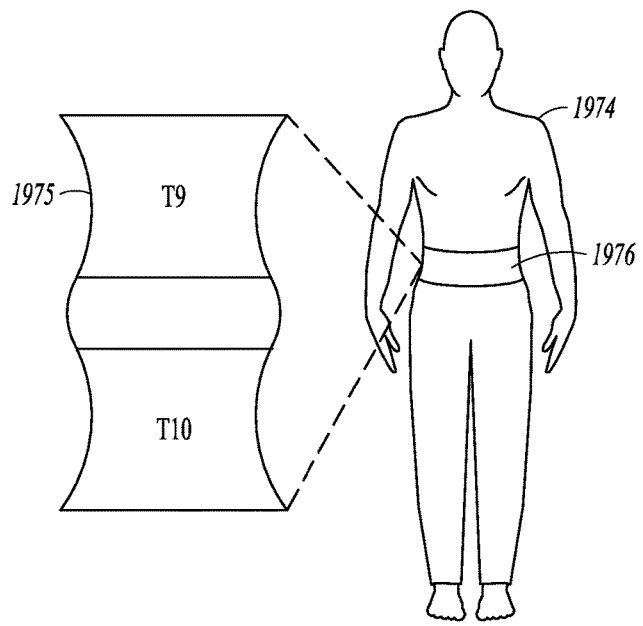
FIG. 19
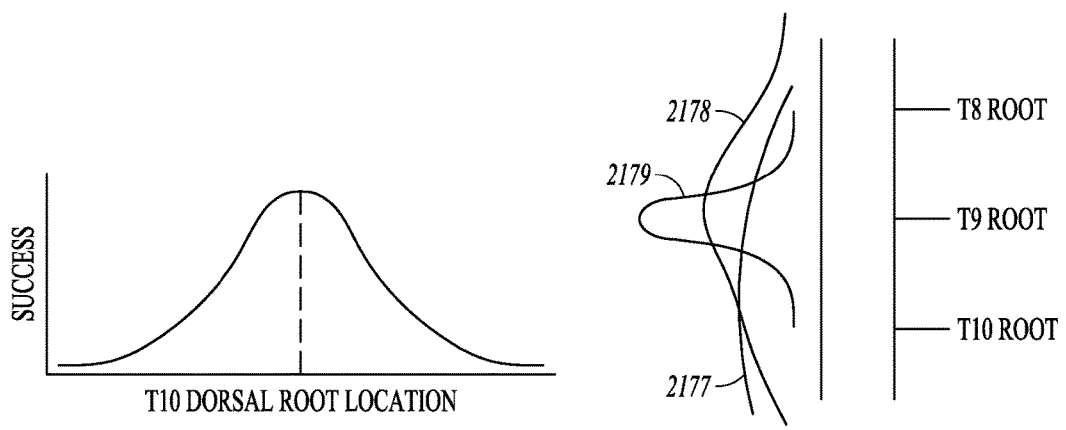
FIG. 20
FIG. 21

SYSTEM AND METHOD FOR DETERMINING THE NEUROLOGICAL POSITION OF EPIDURAL LEADS

TECHNICAL FIELD

This application claims the benefit of priority under 35 U.S.C. §119(e) of U.S. Provisional Patent Application Ser. No. 62/113,654, filed on Feb. 9, 2015, which is herein incorporated by reference in its entirety.

TECHNICAL FIELD

This document relates generally to medical devices, and more particularly, to systems, devices and methods for delivering neural modulation.

BACKGROUND

Neural modulation has been proposed as a therapy for a number of conditions. Often, neural modulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS, by way of example and not limitation, has been used to treat chronic pain syndromes.

Some neural targets may be complex structures with different types of nerve fibers. An example of such a complex structure is the neuronal elements in and around the spinal cord targeted by SCS. This complexity may contribute to difficulties in placing modulation electrodes and difficulties in programming the modulation field(s) in different patients as the optimal placement of the modulation electrodes and the optimal modulation field to treat a specific pain area can vary among patients.

SUMMARY

An example (e.g. "Example 1") of a system may include an electrode arrangement configured for implantation in an epidural space, a neural modulation generator configured to use electrodes in the electrode arrangement to generate modulation fields, at least one storage and a controller operably connected to the neural modulation generator. The at least one storage may store supra-perception threshold dorsal root modulation field parameter data and therapeutic modulation field parameter data, where the therapeutic modulation field parameter data may be different than the supra-perception threshold dorsal root modulation field parameter data. The system may be configured to deliver a placement modulation field from the electrode arrangement in the epidural space to the dorsal roots using the supra-perception threshold dorsal root modulation field parameter data, and deliver a therapeutic modulation field from the electrode arrangement placed in the desired position within the epidural space to a therapeutic neural target using the therapeutic modulation field parameter data.

In Example 2, the subject matter of Example 1 may optionally be configured such that the system includes an implantable device and an external device configured to communicate with the implantable device. The external device may be configured to program the implantable device with the supra-perception threshold dorsal root modulation field parameter data and the therapeutic modulation field parameter data.

In Example 3, the subject matter of Example 2 may optionally be configured such that the system includes a remote service with a database accessible through Internet communication. The service may be configured to receive patient data from a plurality of patients where the patient data may include dorsal root location of the electrode arrangement and corresponding paresthesia generated for the dorsal root location of the electrode arrangement, perform data analytics on the patient data from the plurality of patients, and co-register patients to identify a likelihood of paresthesia for a supra-perception therapy or a likelihood of analgesia for a sub-perception therapy at a dorsal root location.

In Example 4, the subject matter of any one or any combination of Examples 2-3 may optionally be configured such that the external device includes a user interface to receive patient-perception information.

In Example 5, the subject matter of Example 4 may optionally be configured such that the user interface includes a graphical user interface with a body image configured to allow a patient to enter the patient-perception information by selecting one or more regions of the body image.

In Example 6, the subject matter of any one or any combination of Examples 4-5 may optionally be configured such that the patient-perception information includes dorsal root paresthesia.

In Example 7, the subject matter of any one or any combination of Examples 1-6 may optionally be configured such that the therapeutic modulation field does not cause patient-perceived paresthesia.

In Example 8, the subject matter of any one or any combination of Examples 1-7 may optionally be configured such that the therapeutic modulation field has a larger pulse width than the placement modulation field.

In Example 9, the subject matter of any one or any combination of Examples 1-8 may optionally be configured such that the placement modulation field includes anodic monopolar modulation.

In Example 10, the subject matter of any one or any combination of Examples 1-8 may optionally be configured such that the placement modulation field includes cathodic monopolar modulation.

In Example 11, the subject matter of any one or any combination of Examples 1-10 may optionally be configured such that the controller is configured to perform a fitting procedure for the placed electrode arrangement to identify therapeutic modulation parameters for delivering the therapeutic modulation field from the placed electrode arrangement to the therapeutic neural target.

In Example 12, the subject matter of any one or any combination of Examples 1-11 may optionally be configured such that the therapeutic modulation parameters for delivering the therapeutic modulation field from the electrode arrangement in the desired position within the epidural space to the therapeutic neural target includes therapeutic modulation parameters for delivering sub-perception modulation to a neural target selected from the group consisting of: a dorsal column; a dorsal horn; and a dorsal root.

In Example 13, the subject matter of any one or any combination of Examples 1-11 may optionally be configured such that the therapeutic modulation parameters for delivering the therapeutic modulation field from the electrode arrangement in the desired position within the epidural space to the therapeutic neural target includes therapeutic modulation parameters for delivering a modulation field to a dorsal horn.

In Example 14, the subject matter of any one or any combination of Examples 1-11 may optionally be configured such that the therapeutic modulation parameters for delivering the therapeutic modulation field from the electrode arrangement in the desired position within the epidural space to the therapeutic neural target includes therapeutic modulation parameters for delivering a modulation field to a dorsal column.

In Example 15, the subject matter of any one or any combination of Examples 1-11 may optionally be configured such that the system is configured to create an atlas based on neuroanatomy.

An example (e.g. "Example 16") of a method may include inserting an electrode arrangement into an epidural space, and monitoring the electrode position with respect to neuroanatomy to position the electrode arrangement in a desired position within the epidural space. Monitoring may include delivering supra-perception threshold stimulation from the electrode arrangement in the epidural space to dorsal roots, receiving patient-perception information for the supra-perception threshold stimulation delivered to the dorsal roots, and placing the electrode arrangement in the desired position within the epidural space using the patient-perception information.

In Example 17, the subject matter of Example 16 may optionally be configured such that the method includes performing a fitting procedure for the electrode arrangement, after placing the electrode arrangement in the desired position, to identify therapeutic modulation parameters for delivering a therapeutic modulation field from the electrode arrangement to a therapeutic neural target.

In Example 18, the subject matter of Example 17 may optionally be configured such that the method includes delivering therapeutic neural stimulation to the therapeutic neural target using the therapeutic modulation parameters.

An example (e.g. "Example 19") of a method may include performing a placement procedure, including delivering supra-perception threshold modulation from an electrode arrangement in the epidural space to dorsal roots, receiving patient-perception information for the supra-perception threshold modulation delivered to the dorsal roots, and using the patient-perception information to either place the electrode arrangement in a desired position within the epidural space using the patient-perception information or place a supra-perception modulation field to modulate a targeted neuroanatomy. The method may further include delivering therapeutic neural modulation using the electrode arrangement in the desired position within the epidural space or using therapeutic modulation parameters derived from parameters used to place the supra-perception modulation field to modulate the targeted neuroanatomy.

In Example 20, the subject matter of Example 19 may optionally be configured such that the method includes the patient-perception information for the supra-perception threshold modulation includes dorsal root paresthesia.

In Example 21, the subject matter of Example 19 may optionally be configured such that receiving patient-perception information includes using a body image on a user interface to receive the patient-perception information.

In Example 22, the subject matter of Example 19 may optionally be configured such that the patient-perception information for the supra-perception threshold modulation includes a highest level that patient-perceived tingling is felt.

In Example 23, the subject matter of Example 19 may optionally be configured such that the therapeutic neural modulation has a larger pulse width than the supra-perception threshold modulation.

In Example 24, the subject matter of Example 24 may optionally be configured such that the therapeutic neural modulation includes bipolar modulation and the supra-perception threshold stimulation includes monopolar modulation.

In Example 25, the subject matter of Example 19 may optionally be configured such that the supra-perception threshold modulation includes anodic monopolar modulation.

In Example 26, the subject matter of Example 19 may optionally be configured such that the supra-perception threshold modulation includes cathodic monopolar modulation.

In Example 27, the subject matter of Example 19 may optionally be configured such that the method includes performing a fitting procedure, after placing the electrode arrangement in the desired position, for the placed electrode arrangement to identify therapeutic modulation parameters for delivering a therapeutic modulation field to a therapeutic neural target using the electrode arrangement.

In Example 28, the subject matter of Example 19 may optionally be configured such that the method includes collecting and aggregating patient data for a plurality of patients where the patient data includes dorsal root location of the electrode arrangement and corresponding paresthesia generated for the dorsal root location of the electrode arrangement, and co-registering patients to identify a likelihood of paresthesia for a supra-perception therapy or a likelihood of analgesia for a sub-perception therapy at selected dorsal roots.

In Example 29, the subject matter of Example 19 may optionally be configured such that the method includes creating an atlas based on neuroanatomy.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 9 is a schematic view of a single electrical modulation lead implanted within epidural space over approximately the longitudinal midline of the patient's spinal cord.

FIG. 10 illustrates an embodiment where an electrical modulation lead has been implanted within epidural space more laterally with respect to the spinal cord, thereby placing it proximate the dorsal horn of the spinal cord, and the other electrical modulation lead has been implanted within epidural space more medially with respect to the spinal cord, thereby placing it proximate the dorsal column of the spinal cord.

FIG. 11 is a schematic view of the electrical modulation lead showing an example of the fractionalization of the anodic current delivered to the electrodes on the electrical modulation lead.

FIG. 19 illustrates a body image along with an image of bony anatomy associated with spinal column.

FIG. 20 illustrates a plot of therapy success against a dorsal root location.

FIG. 21 illustrates an image that may be illustrated an on a GUI of an external device such as a programmer, for example.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Figure 1:
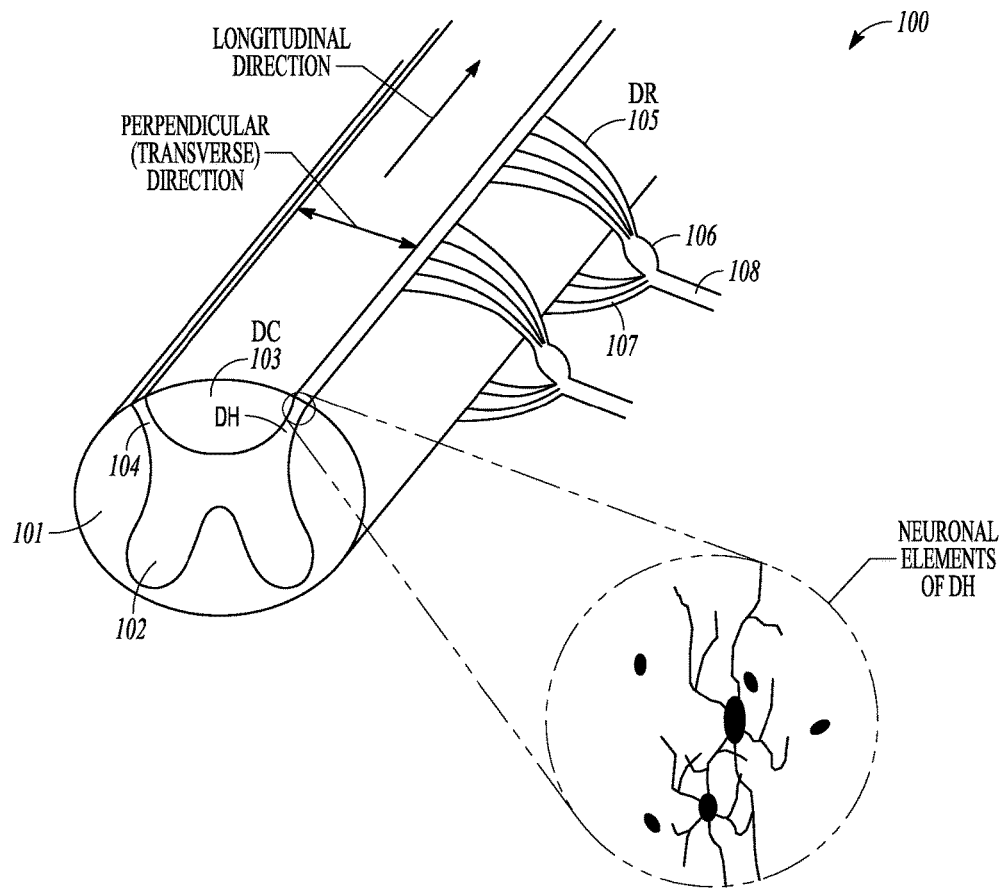
FIG. 1 illustrates a portion of a spinal cord.

Various embodiments described herein involve spinal cord modulation. A brief description of the physiology of the spinal cord is provided herein to assist the reader. FIG. 1 illustrates, by way of example, a portion of a spinal cord 100 including white matter 101 and gray matter 102 of the spinal cord. The gray matter 102 includes cell bodies, synapse, dendrites, and axon terminals. Thus, synapses are located in the gray matter. White matter 101 includes myelinated axons that connect gray matter areas. A typical transverse section of the spinal cord includes a central "butterfly" shaped central area of gray matter 102 substantially surrounded by an ellipse-shaped outer area of white matter 101. The white matter of the dorsal column (DC) 103 includes mostly large myelinated axons that form afferent fibers that run in an axial direction. The dorsal portions of the "butterfly" shaped central area of gray matter are referred to as dorsal horns (DH) 104. In contrast to the DC fibers that run in an axial direction, DH fibers can be oriented in many directions, including perpendicular to the longitudinal axis of the spinal cord. Examples of spinal nerves are also illustrated, including a dorsal root (DR) 105, dorsal root ganglion 106 and ventral root 107. The dorsal root 105 mostly carries sensory signals into the spinal cord, and the ventral root functions as an efferent motor root. The dorsal and ventral roots join to form mixed spinal nerves 108.

SCS has been used to alleviate pain. A therapeutic goal for conventional SCS programming has been to maximize stimulation (i.e., recruitment) of the DC fibers that run in the white matter along the longitudinal axis of the spinal cord and minimal stimulation of other fibers that run perpendicular to the longitudinal axis of the spinal cord (dorsal root fibers, predominantly), as illustrated in FIG. 1. The white matter of the DC includes mostly large myelinated axons that form afferent fibers. While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been targeted for stimulation at an amplitude that provides pain relief. Current implantable neuromodulation systems typically include electrodes implanted adjacent, i.e., resting near, or upon the dura, to the dorsal column of the spinal cord of the patient and along a longitudinal axis of the spinal cord of the patient.

Activation of large sensory DC nerve fibers also typically creates the paresthesia sensation that often accompanies conventional SCS therapy. Some embodiments may deliver supra-perception SCS therapy, such as conventional SCS therapy that creates paresthesia. Although alternative or artifactual sensations, such as paresthesia, are usually tolerated relative to the sensation of pain, patients sometimes report these sensations to be uncomfortable. Some embodiments deliver sub-perception SCS therapy that is therapeutically effective to treat pain, for example, but the patient does not sense the delivery of the modulation field (e.g. paresthesia). Sub-perception therapy may include higher frequency modulation (e.g. about 1500 Hz or above) of the spinal cord that effectively blocks the transmission of pain signals in the afferent fibers in the DC. Some embodiments herein selectively modulate DH tissue or DR tissue over DC tissue to provide sub-perception therapy. Such selective modulation is not delivered at these higher frequencies. For example, the selective modulation may be delivered at frequencies at or less than 1,200 Hz. The selective modulation may be delivered at frequencies at or less than 1,000 Hz in some embodiments. In some embodiments, the selective modulation may be delivered at frequencies at or less than 500 Hz. In some embodiments, the selective modulation may be delivered at frequencies at or less than 350 Hz. In some embodiments, the selective modulation may be delivered at frequencies at or less than 130 Hz. The selective modulation may be delivered at low frequencies (e.g. as low as 2 Hz). The selective modulation may be delivered even without pulses (e.g. 0 Hz) to modulate some neural tissue. By way of example and not limitation, the selective modulation may be delivered within a frequency range selected from the following frequency ranges: 2 Hz to 1,200 Hz; 2 Hz to 1,000 Hz, 2 Hz to 500 Hz; 2 Hz to 350 Hz; or 2 Hz to 130 Hz. Systems may be developed to raise the lower end of any these ranges from 2 Hz to other frequencies such as, by way of example and not limitation, 10 Hz, 20 Hz, 50 Hz or 100 Hz. By way of example and not limitation, it is further noted that the selective modulation may be delivered with a duty cycle, in which stimulation (e.g. a train of pulses) is delivered during a Stimulation ON portion of the duty cycle, and is not delivered during a Stimulation OFF portion of the duty cycle. By way of example and not limitation, the duty cycle may be about 10%±5%, 20%±5%, 30%±5%, 40%±5%, 50%±5% or 60%±5%. For example, a burst of pulses for 10 ms during a Stimulation ON portion followed by 15 ms without pulses corresponds to a 40% duty cycle.

Figure 2:
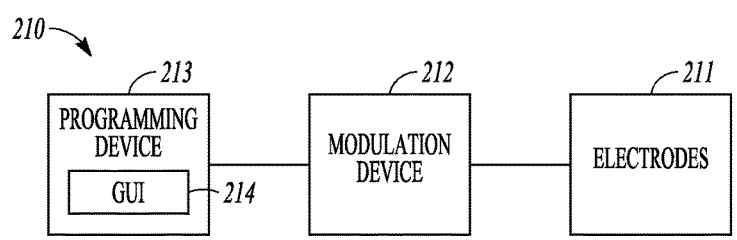
FIG. 2 illustrates, by way of example, an embodiment of a neuromodulation system.

FIG. 2 illustrates an embodiment of a neuromodulation system. The illustrated system 210 includes electrodes 211, a modulation device 212, and a programming device 213. The electrodes 211 are configured to be placed on or near one or more neural targets in a patient. The modulation device 212 is configured to be electrically connected to electrodes 211 and deliver neuromodulation energy, such as in the form of electrical pulses, to the one or more neural targets though electrodes 211. The delivery of the neuromodulation is controlled by using a plurality of modulation parameters, such as modulation parameters specifying the electrical pulses and a selection of electrodes through which each of the electrical pulses is delivered. In various embodiments, at least some parameters of the plurality of modulation parameters are programmable by a user, such as a physician or other caregiver. The programming device 213 provides the user with accessibility to the user-programmable parameters. In various embodiments, the programming device 213 is configured to be communicatively coupled to modulation device via a wired or wireless link. In various embodiments, the programming device 213 includes a graphical user interface (GUI) 214 that allows the user to set and/or adjust values of the user-programmable modulation parameters.

Figure 3:
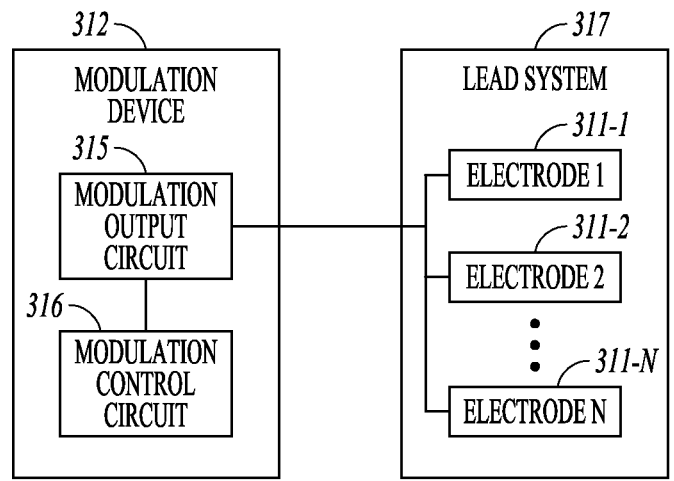
FIG. 3 illustrates, by way of example, an embodiment of a modulation device, such as may be implemented in the neuromodulation system of FIG. 2.

FIG. 3 illustrates an embodiment of a modulation device 312, such as may be implemented in the neuromodulation system 210 of FIG. 2. The illustrated embodiment of the modulation device 312 includes a modulation output circuit 315 and a modulation control circuit 316. Those of ordinary skill in the art will understand that the neuromodulation system 210 may include additional components such as sensing circuitry for patient monitoring and/or feedback control of the therapy, telemetry circuitry and power. The modulation output circuit 315 produces and delivers neuromodulation pulses. The modulation control circuit 316 controls the delivery of the neuromodulation pulses using the plurality of modulation parameters. The lead system 317 includes one or more leads each configured to be electrically connected to modulation device 312 and a plurality of electrodes 311-1 to 311-N distributed in an electrode arrangement using the one or more leads, where N≥2. Each lead may have an electrode array consisting of two or more electrodes, which also may be referred to as contacts. Multiple leads may provide multiple electrode arrays to provide the electrode arrangement. Each electrode is a single electrically conductive contact providing for an electrical interface between modulation output circuit 315 and tissue of the patient. The neuromodulation pulses are each delivered from the modulation output circuit 315 through a set of electrodes selected from the electrodes 311-1 to 311-N. The number of leads and the number of electrodes on each lead may depend on, for example, the distribution of target(s) of the neuromodulation and the need for controlling the distribution of electric field at each target. In one embodiment, by way of example and not limitation, the lead system includes two leads each having eight electrodes. In some embodiments, the lead system may include a paddle lead.

The neuromodulation system may be configured to therapeutically modulate spinal target tissue or other neural tissue. The therapeutic modulation may be supra-perception modulation or sub-perception modulation. As will be described in more detail below, the neuromodulation system may be configured to deliver supra-perception modulation to dorsal roots for use in placing the electrode arrangement in position to deliver a therapy. In addition or as an alternative to delivering supra-perception modulation to dorsal roots for use in placing the electrode arrangement, the neuromodulation system may be configured to deliver supra-perception modulation to dorsal roots for use in programming the modulation field using a placed electrode arrangement. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses. Each electrode configuration, along with the electrical pulse parameters, can be referred to as a "modulation parameter set." Each set of modulation parameters, including fractionalized current distribution to the electrodes (as percentage cathodic current, percentage anodic current, or off), may be stored and combined into a modulation program that can then be used to modulate multiple regions within the patient.

The number of electrodes available combined with the ability to generate a variety of complex electrical pulses, presents a huge selection of modulation parameter sets to the clinician or patient. For example, if the neuromodulation system to be programmed has sixteen electrodes, millions of modulation parameter sets may be available for programming into the neuromodulation system. Furthermore, for example SCS systems may have thirty-two electrodes which exponentially increases the number of modulation parameters sets available for programming. To facilitate such selection, the clinician generally programs the modulation parameters sets through a computerized programming system to allow the optimum modulation parameters to be determined based on patient feedback or other means and to subsequently program the desired modulation parameter sets.

Conventional programming for SCS therapy uses paresthesia to select an appropriate modulation parameter set. The paresthesia induced by the modulation and perceived by the patient should be located in approximately the same place in the patient's body as the pain that is the target of treatment.

When leads are implanted within the patient, an operating room (OR) mapping procedure may be performed to apply electrical modulation to test placement of the leads and/or electrodes, thereby assuring that the leads and/or electrodes are implanted in effective locations within the patient. Various embodiments use a modulation parameter set that includes supra-perception threshold dorsal root modulation field parameter data to intentionally modulate dorsal roots during the placement of the leads and/or electrodes. Various embodiments use a modulation parameter set that includes supra-perception threshold dorsal root modulation field parameter data to intentionally modulate dorsal roots after placement of the lead(s). For example, the supra-perception threshold dorsal root modulation field parameter data may be used to guide subsequent programming of the modulation field(s), or may be used to provide registration and mapping using the dorsal root location and lead location as a reference. One reason why there is so much intrapatient variability in terms of optimal SCS lead placement to treat any specific pain area (e.g. low back) may be that the bony anatomy and neuroanatomy are varied in their spatial relationship from patient to patient. Although neuroanatomy and bony anatomy are related, they can differ. An x-ray can show bony anatomy, but cannot show the spinal cord. Therefore, use of imaging techniques to use the bony anatomy alone to place the lead and/or electrodes may not accurately place the lead and/or electrodes. It may be desirable to think primarily about the neuroanatomy when programming a patient. The dorsal roots have a more predictable and reliable relationship to the spinal bony anatomy than the cord because the neuroforamina through which they travel is small and predictable in location. Dorsal roots are heterogeneous, as they include other fibers than that which is targeted. Therefore, dorsal root paresthesias are normally avoided in SCS since they have an increased likelihood of being uncomfortable.

However, various embodiments described herein use dorsal root paresthesias (or other patient-perceived sensation to the dorsal root modulation) for the purpose of determining the neurological position of the SCS lead(s). The position of the lead(s) is thus determined with respect to neuroanatomy and not just bony anatomy. Therefore, the root location need not be reliable with respect to bony anatomy. There is more predictability and consistency across patients as the foramina, through which the nerve roots travel, are in the same region. Specific programming parameters can be used to elicit and determine the location of the paresthesias that can be attributable to the dorsal roots. For example, some parameters may include low pulse width (e.g. less than 100 µs such as pulse widths within a range from 20 µs to 50 µs), monopolar modulation, anodal fields or cathodal fields. In a monopolar configuration, a case electrode on the IPG may be one of the cathode or anode, and electrode(s) on the lead may be the other one of the cathode or anode. The patient can identify where the dorsal paresthesias are felt to determine the location of the electrode arrangement. For example, the patient may identify the location of the paresthesia on a body image displayed on an external device.

Once the leads are correctly positioned, a fitting procedure, which may be referred to as a navigation session, may be performed to program the external control device, and if applicable the neuromodulation device, with a set of modulation parameters that best addresses the painful site. Thus, the navigation session may be used to pinpoint the volume of activation (VOA) or areas correlating to the pain. The procedure may be implemented to target the tissue during implantation, or after implantation to target the tissue. The exact location is not necessarily determined during the operation. Rather, the device may be programmed to search for the desired modulation target or to refine the location of the desired modulation target. The procedure may be implemented if the leads gradually or unexpectedly move causing the modulation energy to move away from the target site. The supra-perception modulation of the dorsal roots may be part of this calibration and search process after implant or after suspected lead movement. By reprogramming the neuromodulation device (typically by independently varying the modulation energy on the electrodes), the VOA can often be moved back to the effective pain site without having to re-operate on the patient in order to reposition the lead and its electrode array. When adjusting the VOA relative to the tissue, it is desirable to make small changes in the proportions of current, so that changes in the spatial recruitment of nerve fibers will be perceived by the patient as being smooth and continuous and to have incremental targeting capability.

Figure 4:
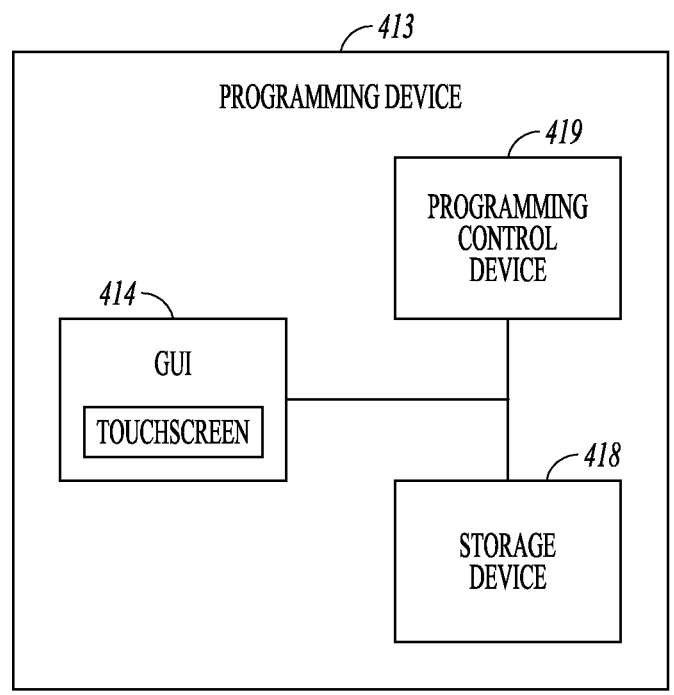
FIG. 4 illustrates, by way of example, an embodiment of a programming device, such as may be implemented as the programming device in the neuromodulation system of FIG. 2.

FIG. 4 illustrates an embodiment of a programming device 413, such as may be implemented as the programming device 213 in the neuromodulation system of FIG. 2. The programming device 413 includes a storage device 418, a programming control circuit 419, and a GUI 414. The programming control circuit 419 generates the plurality of modulation parameters that controls the delivery of the neuromodulation pulses according to the pattern of the neuromodulation pulses. In various embodiments, the GUI 414 includes any type of presentation device, such as interactive or non-interactive screens, and any type of user input devices that allow the user to program the modulation parameters, such as touchscreen, keyboard, keypad, touchpad, trackball, joystick, and mouse. The storage device 418 may store, among other things, modulation parameters to be programmed into the modulation device. The modulation parameters may be organized into one or more sets of modulation parameters. Thus, some embodiments may provide supra-perception threshold dorsal root modulation field parameter data in a set of modulation parameters and may provide therapeutic modulation field parameter data in another set of modulation parameters. The programming device 413 may transmit the plurality of modulation parameters to the modulation device. In some embodiments, the programming device 413 may transmit power to the modulation device. The programming control circuit 419 may generate the plurality of modulation parameters. In various embodiments, the programming control circuit 419 may check values of the plurality of modulation parameters against safety rules to limit these values within constraints of the safety rules.

In various embodiments, circuits of neuromodulation, including its various embodiments discussed in this document, may be implemented using a combination of hardware, software and firmware. For example, the circuit of GUI, modulation control circuit, and programming control circuit, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 5:
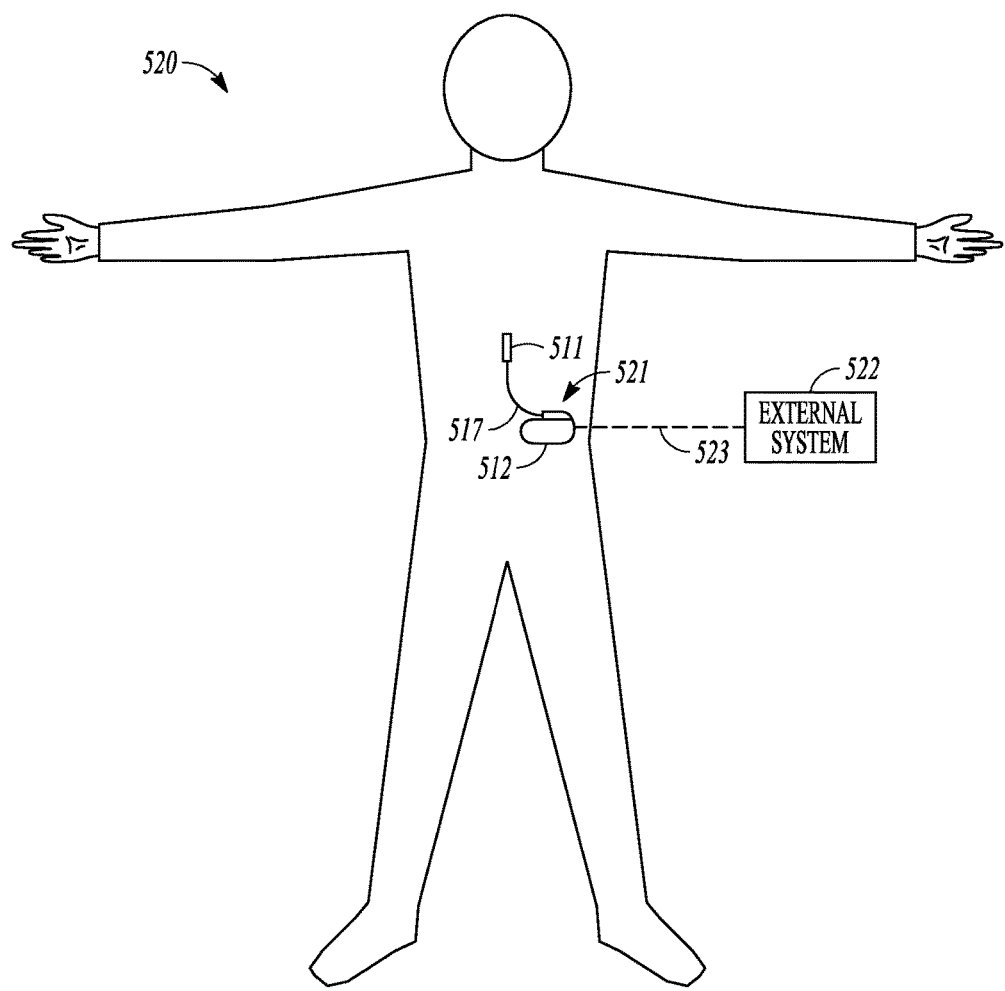
FIG. 5 illustrates, by way of example, an implantable neuromodulation system and portions of an environment in which system may be used.

FIG. 5 illustrates, by way of example, an implantable neuromodulation system and portions of an environment in which system may be used. The system is illustrated for implantation near the spinal cord. The system 520 includes an implantable system 521, an external system 522, and a telemetry link 523 providing for wireless communication between implantable system 521 and external system 522. The implantable system is illustrated as being implanted in the patient's body. The implantable system 521 includes an implantable modulation device (also referred to as an implantable pulse generator, or IPG) 512, a lead system 517, and electrodes 511. The lead system 517 includes one or more leads each configured to be electrically connected to the modulation device 512 and a plurality of electrodes 511 distributed in the one or more leads. In various embodiments, the external system 402 includes one or more external (non-implantable) devices each allowing a user (e.g. a clinician or other caregiver and/or the patient) to communicate with the implantable system 521. In some embodiments, the external system 522 includes a programming device intended for a clinician or other caregiver to initialize and adjust settings for the implantable system 521 and a remote control device intended for use by the patient. For example, the remote control device may allow the patient to turn a therapy on and off and/or adjust certain patient-programmable parameters of the plurality of modulation parameters.

The neuromodulation lead(s) of the lead system 517 may be placed adjacent, i.e., resting near, or upon the dura, adjacent to the spinal cord area to be stimulated. For example, the neuromodulation lead(s) may be implanted along a longitudinal axis of the spinal cord of the patient. Due to the lack of space near the location where the neuromodulation lead(s) exit the spinal column, the implantable modulation device 512 may be implanted in a surgically-made pocket either in the abdomen or above the buttocks, or may be implanted in other locations of the patient's body. The lead extension(s) may be used to facilitate the implantation of the implantable modulation device 512 away from the exit point of the neuromodulation lead(s).

Figure 6:
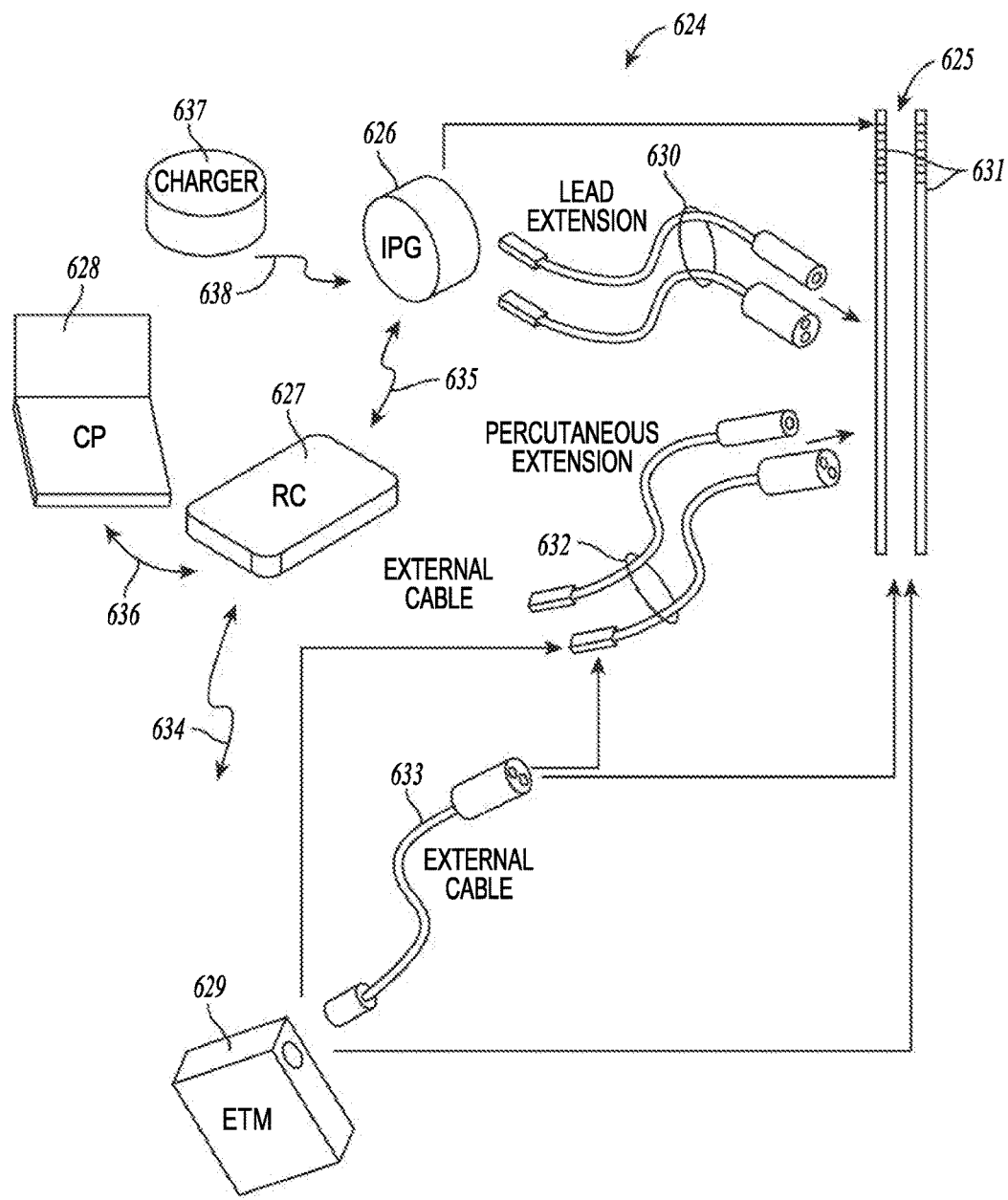
FIG. 6 illustrates, by way of example, an embodiment of a Spinal Cord Stimulation (SCS) system, which also may be referred to as a Spinal Cord Modulation (SCM) system.

FIG. 6 illustrates, by way of example, an embodiment of a SCS system, which also may be referred to as a Spinal Cord Modulation (SCM) system. The SCS system 624 may generally include a plurality (illustrated as two) of implantable neuromodulation leads 625, an implantable pulse generator (IPG) 626, an external remote controller RC 627, a clinician's programmer (CP) 628, and an external trial modulator (ETM) 629. The IPG 626 may be physically connected via one or more percutaneous lead extensions 630 to the neuromodulation leads 625, which carry a plurality of electrodes 631. The electrodes, when implanted in a patient, form an electrode arrangement. As illustrated, the neuromodulation leads 625 may be percutaneous leads with the electrodes arranged in-line along the neuromodulation leads. Any suitable number of neuromodulation leads can be provided, including only one, as long as the number of electrodes is greater than two (including the IPG case function as a case electrode) to allow for lateral steering of the current. Alternatively, a surgical paddle lead can be used in place of one or more of the percutaneous leads. The IPG 626 includes pulse generation circuitry that delivers electrical modulation energy in the form of a pulsed electrical waveform (i.e., a temporal series of electrical pulses) to the electrodes in accordance with a set of modulation parameters.

The ETM 629 may also be physically connected via the percutaneous lead extensions 632 and external cable 633 to the neuromodulation leads 625. The ETM 629 may have similar pulse generation circuitry as the IPG 626 to deliver electrical modulation energy to the electrodes accordance with a set of modulation parameters. The ETM 629 is a non-implantable device that may be used on a trial basis after the neuromodulation leads 625 have been implanted and prior to implantation of the IPG 626, to test the responsiveness of the modulation that is to be provided. Functions described herein with respect to the IPG 626 can likewise be performed with respect to the ETM 629.

The RC 627 may be used to telemetrically control the ETM 629 via a bi-directional RF communications link 634. The RC 627 may be used to telemetrically control the IPG 626 via a bi-directional RF communications link 635. Such control allows the IPG 626 to be turned on or off and to be programmed with different modulation parameter sets. The IPG 626 may also be operated to modify the programmed modulation parameters to actively control the characteristics of the electrical modulation energy output by the IPG 626. A clinician may use the CP 628 to program modulation parameters into the IPG 626 and ETM 629 in the operating room and in follow-up sessions.

The CP 628 may indirectly communicate with the IPG 626 or ETM 629, through the RC 627, via an IR communications link 636 or other link. The CP 628 may directly communicate with the IPG 626 or ETM 629 via an RF communications link or other link (not shown). The clinician detailed modulation parameters provided by the CP 628 may also be used to program the RC 627, so that the modulation parameters can be subsequently modified by operation of the RC 627 in a stand-alone mode (i.e., without the assistance of the CP 628). Various devices may function as the CP 628. Such devices may include portable devices such as a lap-top personal computer, mini-computer, personal digital assistant (PDA), tablets, phones, or a remote control (RC) with expanded functionality. Thus, the programming methodologies can be performed by executing software instructions contained within the CP 628. Alternatively, such programming methodologies can be performed using firmware or hardware. In any event, the CP 628 may actively control the characteristics of the electrical modulation generated by the IPG 626 to allow the desired parameters to be determined based on patient feedback or other feedback and for subsequently programming the IPG 626 with the desired modulation parameters. To allow the user to perform these functions, the CP 628 may include a user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g. CP) may be programmed to provide display screen(s) that allow the clinician to, among other functions, select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical modulation energy output by the neuromodulation leads, and select and program the IPG with modulation parameters in both a surgical setting and a clinical setting. The external device(s) (e.g. CP and/or RC) may be configured to communicate with other device(s), including local device(s) and/or remote device(s). For example, wired and/or wireless communication may be used to communicate between or among the devices.

An external charger 637 may be a portable device used to transcutaneously charge the IPG via a wireless link such as an inductive link 638. Once the IPG has been programmed, and its power source has been charged by the external charger or otherwise replenished, the IPG may function as programmed without the RC or CP being present.

Figure 7:
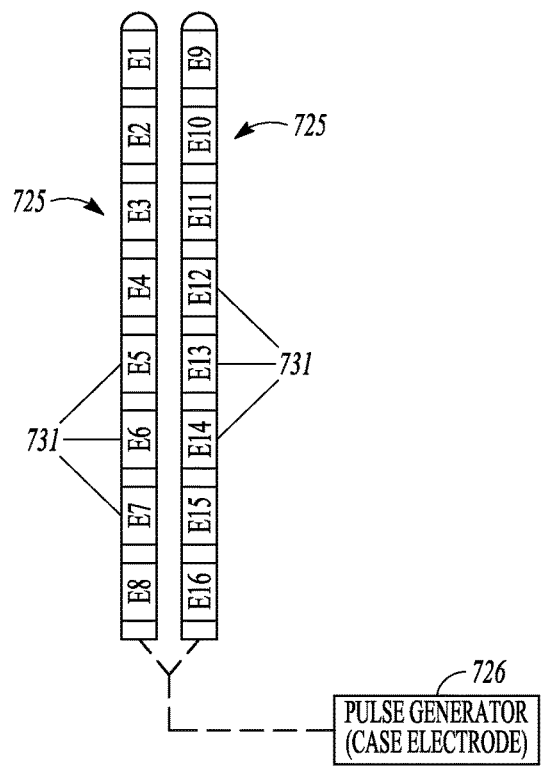
FIG. 7 illustrates, by way of example, some features of the neuromodulation leads and a pulse generator.

FIG. 7 illustrates, by way of example, some features of the neuromodulation leads 725 and a pulse generator 726. The pulse generator 726 may be an implantable device (IPG) or may be an external device such as may be used to test the electrodes during an implantation procedure. In the illustrated example, one of the neuromodulation leads has eight electrodes (labeled E1-E8), and the other neuromodulation lead has eight electrodes (labeled E9-E16). The actual number and shape of leads and electrodes may vary for the intended application. An implantable pulse generator (IPG) may include an outer case for housing the electronic and other components. The outer case may be composed of an electrically conductive, biocompatible material, such as titanium, that forms a hermetically-sealed compartment wherein the internal electronics are protected from the body tissue and fluids. In some cases, the outer case may serve as an electrode (e.g. case electrode). The IPG may include electronic components, such as a controller/processor (e.g., a microcontroller), memory, a battery, telemetry circuitry, monitoring circuitry, modulation output circuitry, and other suitable components known to those skilled in the art. The microcontroller executes a suitable program stored in memory, for directing and controlling the neuromodulation performed by IPG. Electrical modulation energy is provided to the electrodes in accordance with a set of modulation parameters programmed into the pulse generator. The electrical modulation energy may be in the form of a pulsed electrical waveform. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (which may be measured in milliamps or volts depending on whether the pulse generator supplies constant current or constant voltage to the electrode array), pulse width (which may be measured in microseconds), pulse rate (which may be measured in pulses per second), and burst rate (which may be measured as the modulation on duration X and modulation off duration Y). Electrodes that are selected to transmit or receive electrical energy are referred to herein as "activated," while electrodes that are not selected to transmit or receive electrical energy are referred to herein as "non-activated."

Electrical modulation occurs between or among a plurality of activated electrodes, one of which may be the IPG case. The system may be capable of transmitting modulation energy to the tissue in a monopolar or multipolar (e.g., bipolar, tripolar, etc.) fashion. Monopolar modulation occurs when a selected one of the lead electrodes is activated along with the case of the IPG, so that modulation energy is transmitted between the selected electrode and case. Any of the electrodes E1-E16 and the case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the k timing channels. The IPG may be operated in a mode to deliver electrical modulation energy that is therapeutically effective and causes the patient to perceive delivery of the energy (e.g. therapeutically effective to relieve pain with perceived paresthesia), and may be operated in a sub-perception mode to deliver electrical modulation energy that is therapeutically effective and does not cause the patient to perceive delivery of the energy (e.g. therapeutically effective to relieve pain without perceived paresthesia).

The IPG may be configured to individually control the magnitude of electrical current flowing through each of the electrodes. For example, a current generator may be configured to selectively generate individual current-regulated amplitudes from independent current sources for each electrode. In some embodiments, the pulse generator may have voltage regulated outputs. While individually programmable electrode amplitudes are desirable to achieve fine control, a single output source switched across electrodes may also be used, although with less fine control in programming. Neuromodulators may be designed with mixed current and voltage regulated devices.

As identified earlier, when leads are implanted within the patient, an operating room (OR) mapping procedure may be performed to apply electrical modulation to test placement of the leads and/or electrodes, thereby assuring that the leads and/or electrodes are implanted in effective locations within the patient. Various embodiments use a modulation parameter set that includes supra-perception threshold dorsal root modulation field parameter data to intentionally modulate dorsal roots during the placement of the leads and/or electrodes. One reason why there is so much intrapatient variability in terms of optimal SCS lead placement to treat any specific pain area (e.g. low back) may be that the bony anatomy and neuroanatomy are varied in their spatial relationship from patient to patient.

Figure 8:
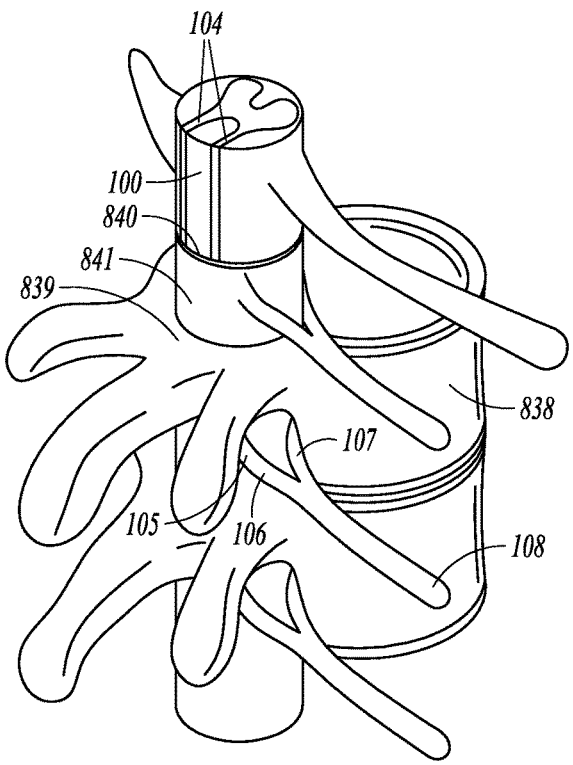
FIG. 8 illustrates a partial view of both neuroanatomy and bony anatomy of the spinal column.
Figure 12A:
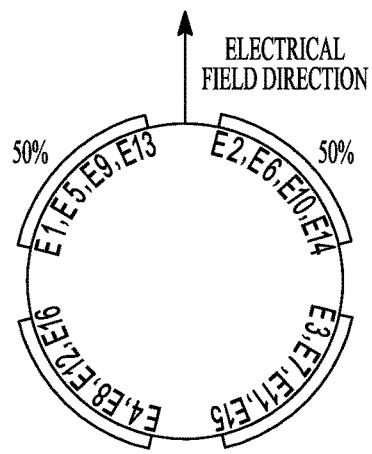
FIGS. 12A-12C and 13A-13C illustrate, by way of example, neural modulation leads in which the electrodes may take the form of segmented electrodes that are circumferentially and axially disposed about the neuromodulation leads.
Figure 12B:
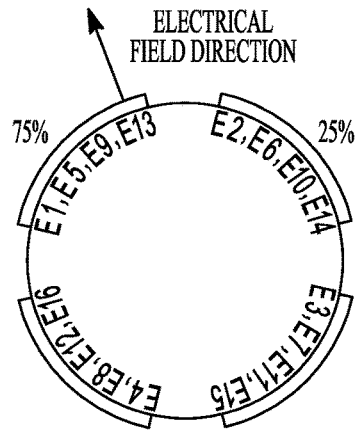
Figure 12C:
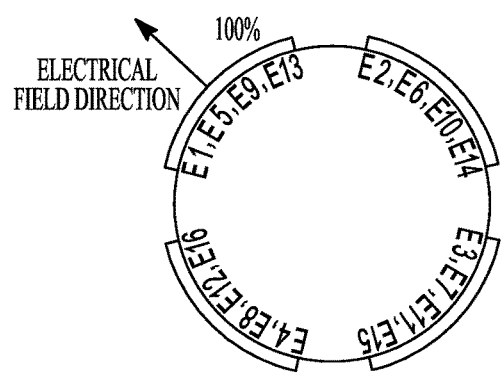
Figure 13A:
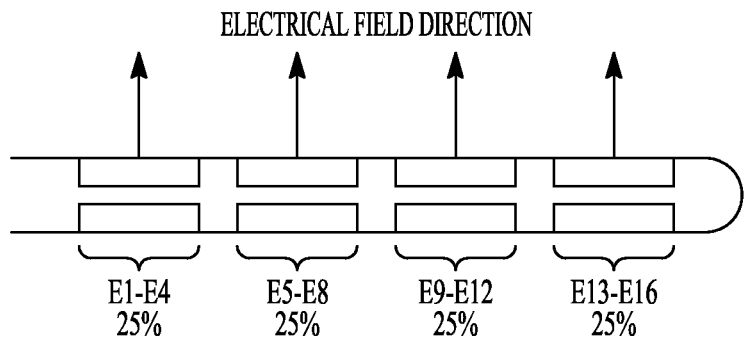
Figure 13B:
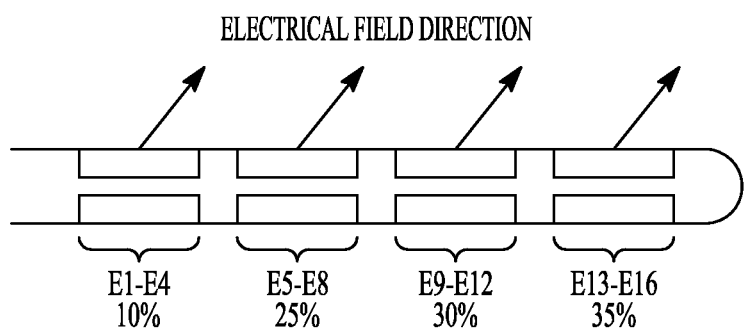
Figure 13C:
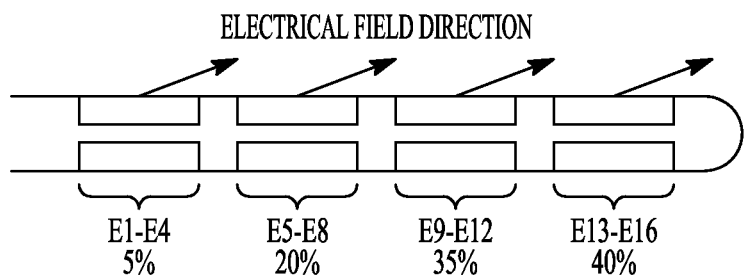

FIG. 8 illustrates, for the convenience of the reader, a partial view of both neuroanatomy and bony anatomy of the spinal column. The neuroanatomy includes the spinal cord 100 such as was illustrated in FIG. 1. The neuroanatomy also includes the dorsal horn 104, the dorsal root 105, the dorsal root ganglion 106, the ventral root 107, and the mixed spinal nerve root 108. The bony anatomy refers to the vertebrae that includes a vertebral body 838 and a bony ring 839 attached to the vertebral body 838. The stacked vertebrae provide a vertebral canal that protects the spinal cord 100. Nerve roots branch off and exit the spine on both sides through spaces ("intervertebral foramen") between the vertebra. The spinal cord is surrounded by dura matter 840, which holds spinal fluid that surrounds the spinal cord 100. The space between the walls and the dura matter of the vertebral canal is referred to as epidural space 841.

The electrode arrangement may be inserted into the epidural space and positioned at a desired location along the spinal cord 100. Various embodiments may use current fractionalization to provide desirable modulation fields to target the dorsal roots with supra-perception modulation, such as may be used to place a lead or to place the modulation field or to map the neurological positions, and to provide desirable modulation fields to deliver therapeutic modulation to the neural elements in and/or near the spinal cord.

FIGS. 9-12C illustrate, by way of example, a difference in electrical field strength in the longitudinal and transverse directions when the current is fractionalized such that the electrical field in the longitudinal direction generated by the fractionalized current delivered to each electrode is approximately equal. Thus, different neural tissue (e.g. dorsal root, dorsal column, dorsal horn) may be targeted by controlling direction of the electric field.

FIG. 9 is a schematic view of a single electrical modulation lead 942 implanted within epidural space over approximately the longitudinal midline of the patient's spinal cord 100. It is understood that additional leads or lead paddle(s) may be used, such as may be used to provide a wider electrode arrangement and/or to provide the electrodes closer to dorsal horn elements, and that these electrode arrays also may implement fractionalized current. FIG. 10 illustrates an embodiment where an electrical modulation lead 1043 has been implanted within epidural space more laterally with respect to the spinal cord, thereby placing it proximate the dorsal horn of the spinal cord, and the other electrical modulation lead 1044 has been implanted within epidural space more medially with respect to the spinal cord, thereby placing it proximate the dorsal column of the spinal cord 100. Placement of the lead more proximate to the DH than the DC may be desirable to preferentially stimulate DH elements over DC neural elements for a sub-perception therapy. Any other plurality of leads or a multiple column paddle lead can also be used.

FIG. 11 is a schematic view of the electrical modulation lead 1145 showing an example of the fractionalization of the anodic current delivered to the electrodes on the electrical modulation lead. These figures illustrate fractionalization using monopolar modulation where a case electrode of the IPG is the only cathode, and carries 100% of the cathodic current. The fractionalization of the anodic current shown in FIG. 11 does not deliver an equal amount of current to each electrode 1146, because this embodiment takes into account electrode/tissue coupling differences, which are the differences in how the tissue underlying each electrode reacts to electrical modulation. Also, the ends of the portion of the electrical modulation lead include electrodes having lower gradient in the longitudinal direction. The magnitude of the electrical field tapers down at the ends of the electrical modulation lead. Fractionalization of the current to the electrodes is controlled such that the tissue underlying each electrode in the middle portion of the electrical modulation lead reacts approximately equally to the electrical modulation, or tissue activation underlying each electrode are eliminated. However, the resulting fractionalization is not equal. In the embodiment shown in FIG. 11, fractionalization of the current to the middle electrodes varies from 10% to 18%, reflecting the variation in the tissue underlying those electrodes. The fractionalization across the electrical modulation lead can vary in any manner as long as the total of fractionalized currents equals 100%. Various embodiments may implement a programmed algorithm to determine the appropriate fractionalization to achieve a desired modulation field property (e.g. constant electric field, or constant electric field magnitude, or constant voltage).

FIGS. 12A-12C and 13A-13C illustrate, by way of example, neural modulation leads in which the electrodes may take the form of segmented electrodes that are circumferentially and axially disposed about the neuromodulation leads. By way of non-limiting example, each neuromodulation lead may carry sixteen electrodes, arranged as four rings of electrodes (the first ring consisting of electrodes E1-E4; the second ring consisting of electrodes E5-E8; the third ring consisting of electrodes E9-E12; and the fourth ring consisting of electrodes E13-E16) or four axial columns of electrodes (the first column consisting of electrodes E1, E5, E9, and E13; the second column consisting of electrodes E2, E6, E10, and E14; the third column consisting of electrodes E3, E7, E11, and E15; and the fourth column consisting of electrodes E4, E8, E12, and E16). The actual number and shape of leads and electrodes may vary according to the intended application.

The SCS system may be used to deliver electrical energy to the spinal cord of the patient using electrical fields having different orientations, also as generally illustrated in FIGS. 12A-12C and 13A-13C. The orientation of the electrical field may be selected to target the directions/orientations of the dorsal roots for the supra-perception dorsal root modulation used to place the electrode array, and may be selected to target the different directions/orientations of other neural elements for therapeutic modulation. To generate electrical fields in different medio-lateral directions, the electrodes may have different current fractionalizations in the radial direction. Although it is desirable that the electrical fields preferentially stimulate DH and/or DR elements over the DC elements, as discussed above, the electrical fields may still be oriented in different rostro-caudal directions (i.e., the direction of the electrical fields as projected on a longitudinal plane through the spinal cord). To generate electrical fields in different rostro-caudal directions, the electrodes may have different current fractionalizations in the longitudinal direction.

The SCS system may be configured to deliver different electrical fields to achieve a temporal summation of modulation in the DH elements. The electrical fields can be generated respectively on a pulse-by-pulse basis. For example, a first electrical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields may be rotated or cycled through multiple times under a timing scheme, where each field is implemented using a timing channel. The electrical fields may be generated at a continuous pulse rate, or may be bursted on and off. Furthermore, the interpulse interval (i.e., the time between adjacent pulses), pulse amplitude, and pulse duration during the electrical field cycles may be uniform or may vary within the electrical field cycle.

Dorsal root paresthesias are generally avoided in therapeutic SCS since these dorsal root paresthesias have an increased likelihood of being uncomfortable. Some modulation parameters can be controlled to decrease the likelihood of unintentionally capturing dorsal roots during therapeutic SCS using epidural leads. For example, longer pulse widths are less likely to capture dorsal roots, and bipolar modulation is less likely to capture dorsal roots than monopolar modulation. Also the position of the electrodes as well as the direction of the modulation field can be controlled to avoid modulation of the dorsal roots during therapeutic SCS.

However, dorsal root paresthesias can be helpful to determine the neurological position of the electrode arrangement with respect to the dorsal roots. Specific modulation parameter sets can be used to provide supra-perception modulation of dorsal roots to elicit and determine the location of the paresthesias that are attributable to dorsal roots. Such programming parameters may direct the modulation fields toward the dorsal roots, may have shorter pulse widths that are more likely to modulate dorsal roots, and/or may use monopolar modulation to increase the likelihood of modulation dorsal roots. A goal of the supra-perception modulation of the dorsal roots, for either therapy delivery or mapping, is to maximize the ratio of the dorsal column threshold to the dorsal root threshold.

Figure 14:
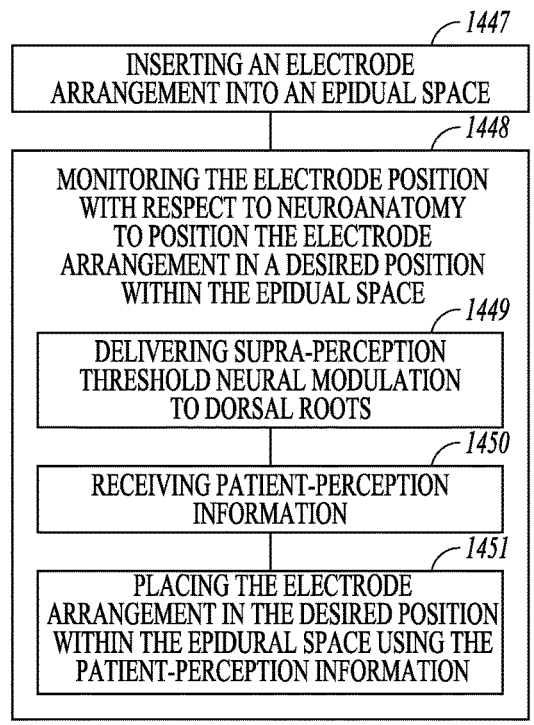
FIGS. 14-16 illustrate examples of methods that involves determining the neurological position of epidural leads.

FIG. 14 illustrates an example of a method that involves determining the neurological position of epidural leads. The illustrated method may include inserting an electrode arrangement into an epidural space 1447, and monitoring the position with respect to neuroanatomy to position the electrode arrangement in a desired position within the epidural space 1448. The electrode arrangement may include electrodes on one or more leads that are inserted into the epidural space for placement in a desired position to deliver therapeutic modulation. This placement process may be referred to as an electrode placement procedure. Monitoring the position may include delivering supra-perception threshold neural modulation from the electrode arrangement in the epidural space to dorsal roots 1449, receiving patient-perception information for the supra-perception threshold modulation delivered to the dorsal roots 1450, and placing the electrode arrangement in a desired position within the epidural space using the patient-perception information 1451. The received patient-perception information for the supra-perception threshold modulation delivered to the dorsal roots 1450 provides a measure of the neurological position of the epidural leads.

Figure 15:
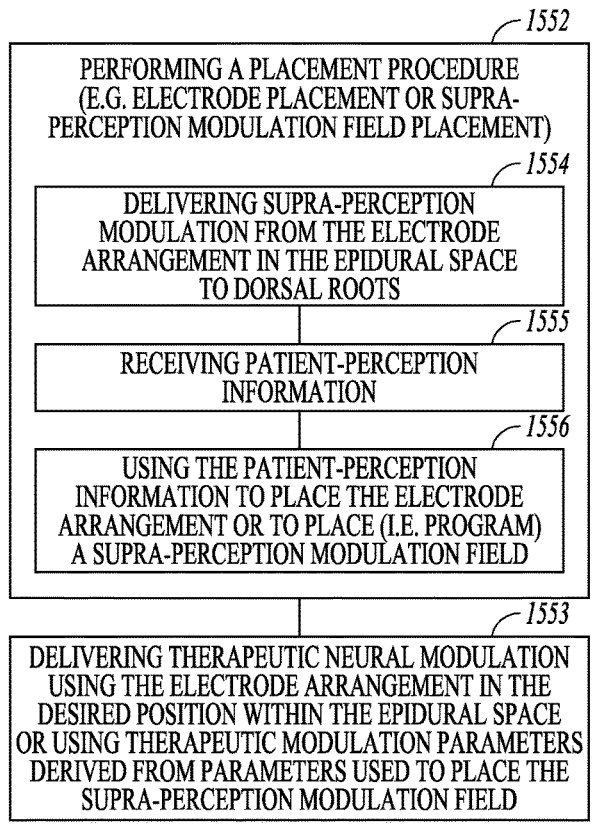

FIG. 15 illustrates an example of a method that involves determining the neurological position of epidural leads. The illustrated method may include performing a placement procedure 1552. The placement procedure may include either or both of an electrode placement procedure for placing an electrode arrangement in a desired position with respect to neuroanatomy, or a supra-perception modulation field placement for modulating dorsal horn tissue, which is perceptible to the patient, to identify a location of targeted neuroanatomy. The method may further include delivering therapeutic neural modulation using the electrode arrangement in the desired position within the epidural space or using therapeutic modulation parameters derived from parameters used to place the supra-perception modulation field 1553. Performing a placement procedure 1552 may include delivering supra-perception threshold modulation from the electrode arrangement in the epidural space to dorsal roots 1554, receiving patient-perception information for the supra-perception threshold modulation delivered to the dorsal roots 1555, and using the patient-perception information to place the electrode arrangement in a desired position within the epidural space or to place a supra-perception modulation field to modulate a targeted neuroanatomy 1556. The received patient-perception information for the supra-perception threshold modulation delivered to the dorsal roots 1555 provides a measure of the neurological position of the epidural leads.

For example, an external device such as a tablet personal computer may be used to program the modulation settings. The same external device or another device may be used to present a body image on a GUI, and to prompt the patient asked to record on the body image the highest level, dermatomally, that they feel tingling. Then, using normal programming parameters, programming is completed and the final settings are activated for the patient to draw where on the body they feel tingling. The modulation lead may span several dorsal roots. For example, the electrode arrangement may span across three segments or dermatome. Thus, different results may be obtained depending on the specific location of the modulation within the array. The modulation field may be trolled along the array to modulate different neural targets along the spinal column. Determining when the changes occur in the results during the trolling may be used to help fractionalize the current for the SCS therapy.

Figure 16:
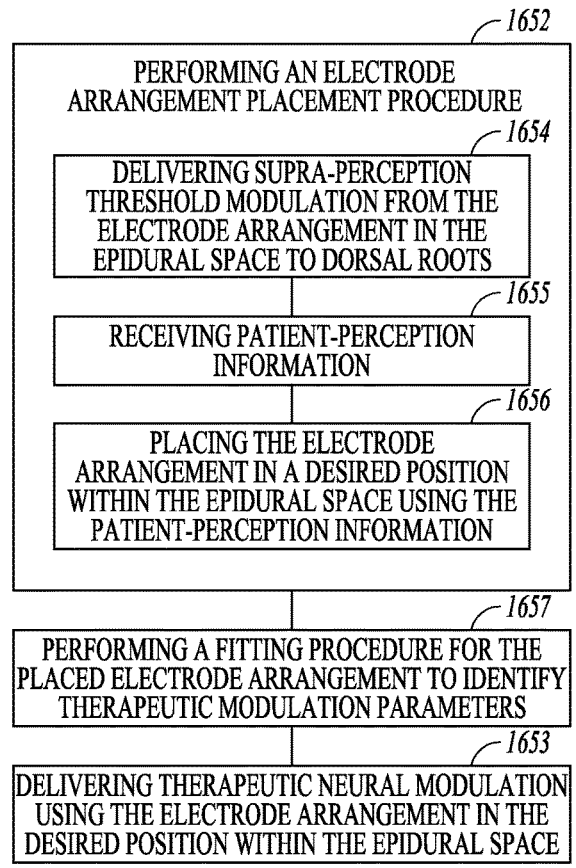

FIG. 16 illustrates an example of a method that involves determining the neurological position of epidural leads. The illustrated method may include performing an electrode arrangement placement procedure 1652 and delivering therapeutic neural modulation using the electrode arrangement in the desired position within the epidural space 1653. Performing an electrode arrangement placement procedure 1652 may include delivering supra-perception threshold modulation from the electrode arrangement in the epidural space to dorsal roots 1654, receiving patient-perception information for the supra-perception threshold modulation delivered to the dorsal roots 1655, and placing the electrode arrangement in a desired position within the epidural space using the patient-perception information 1656. The received patient-perception information for the supra-perception threshold modulation delivered to the dorsal roots 1655 provides a measure of the neurological position of the epidural lead. The method illustrated in FIG. 16 also includes performing a fitting procedure for the placed electrode arrangement to identify the therapeutic modulation parameters 1657. Thus, after the electrode arrangement has been placed using the patient-perception information for the supra-perception modulation delivered to the dorsal roots, the fitting procedure may be used to identify desirable therapeutic modulation parameters. The fitting procedure may use supra-perception modulation of dorsal roots to identify position of neuroanatomy, and then may be used to pinpoint the VOA that corresponds to areas correlating to pain. For conventional SCS therapy that causes paresthesia, for example, the fitting procedure may involve a process where the modulation parameters are adjusted to cause the areas of paresthesia to overlap the area of pain. A fitting procedure for sub-perception SCS may also use supra-perception modulation parameters that generate paresthesia and those supra-perception modulation parameters may be adjusted to generate the paresthesia at a desired location. Subsequently, sub-perception modulation parameters may be programmed to perform the sub-perception SCS.

Figure 17:
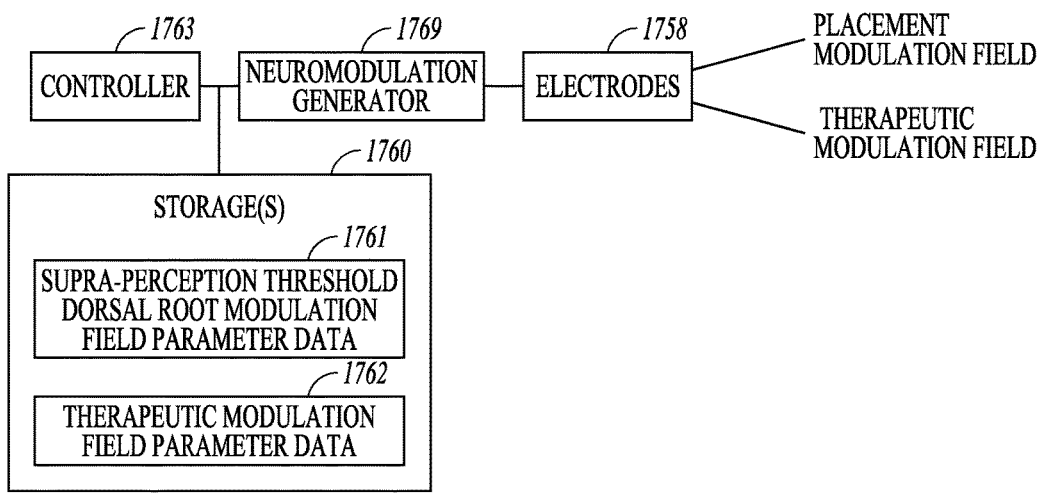
FIG. 17 illustrates an example of a system that involves determining the neurological position of epidural leads using supra-perception dorsal root modulation.

FIG. 17 illustrates an example of a system that involves determining the neurological position of epidural leads using supra-perception dorsal root modulation. The illustrated system may include an electrode arrangement 1758. The electrode arrangement 1758 may be configured for implantation in an epidural space. For example, the electrodes may be on one or more epidural leads. The system may further include a neural modulation generator 1759 configured to use electrodes in the electrode arrangement to generate modulation fields. The system may further include at least one storage 1760 configured to store supra-perception threshold dorsal root modulation field parameter data 1761 and therapeutic modulation field parameter data 1762. The therapeutic modulation field parameter data is different than the supra-perception threshold dorsal root modulation field parameter data, as the therapeutic modulation does not cause supra-perception modulation of the dorsal roots. The system may include a controller 1763 operably connected to the neural modulation generator 1759, and the system may be configured to deliver a placement modulation field from the electrode arrangement in the epidural space to the dorsal roots using the supra-perception threshold dorsal root modulation field parameter data and deliver a therapeutic modulation field from the electrode arrangement placed in the desired position within the epidural space to a therapeutic neural target using the therapeutic modulation field parameter data. The placement modulation field may be used in placing the electrode arrangement within the epidural space in a desired neurological position. The placement modulation field may be used in placing (i.e. programming) the modulation field in a desired neurological position.

The illustrated system may be implemented using implantable and external devices. The storage(s) 1760 may be one or more physical storages in the implantable and/or external devices. The external device may be used to program the supra-perception threshold dorsal root modulation field parameter data 1761 and therapeutic modulation field parameter data 1762 into the implantable device. The implantable device may be configured to simultaneously store both the supra-perception threshold dorsal root modulation field parameter data 1761 and therapeutic modulation field parameter data 1762, or may be configured to be programmed with data 1761 and without data 1762, and then be programmed with data 1762 and without data 1761.

Typically, the SCS therapy does not deliver supra-perception dorsal root modulation as such modulation is generally too uncomfortable for use in a therapy. Such modulation may be uncomfortable because the abdomen is stimulated. However, a therapy may intentionally modulate dorsal roots to target specific dermatomes that do not include the abdomen. Rather the supra-perception dorsal root modulation is used to get a sign post of the lead location with respect to the neuroanatomy. Therefore, the dorsal root modulation field parameter data 1761 is different than the therapeutic modulation field parameter data for typical SCS therapy.

The supra-perception dorsal root modulation may be used to determine a desirable location for the electrode arrangement for the SCS therapy. The SCS therapy may include sub-perception SCS or supra-perception SCS. Sub-perception SCS may include sub-perception modulation of the dorsal column or the dorsal horn or the dorsal roots. Supra-perception SCS may include supra-perception modulation of neural elements in and around the spinal cord, but excludes supra-perception modulation of the dorsal roots as such modulation is typically too uncomfortable for the patient because of the heterogeneous nature of the dorsal roots.

Big data analytics can be used to identify where modulation is located and where paresthesias are felt to create an atlas based on neuroanatomy rather than bony anatomy. If data is aggregated for many patients, it is possible to generate correlations between 'dorsal root location' of leads and the paresthesia generated with those leads. Data analytics techniques could be used to co-register many patients to the 'dorsal root' axis and create histograms of paresthesia likelihood. Mapping the registered nerve location may be particularly helpful with sub-perception modulation, as the patient is not able to perceive paresthesia or other physiological response that could be used to identify the location of the modulation field. Such a map used for sub-perception modulation may be referred to as an analgesia likelihood map rather than a paresthesia likelihood map.

Data can be collected for a single patient using a number of different processes. By way of example and not limitation, the processes may include 1) only collecting data using monopolar configurations at the top and bottom of the electrode arrangement (e.g. lead array), 2) using monopolar configurations at the top, middle and bottom of the electrode arrangement (or a number of other positions along the electrode arrangement), or 3) trolling down the electrode arrangement and capturing new drawings when a threshold of minimum change is achieved from prior settings. Dorsal root paresthesia could be measured either using maximum comfortable settings or at the lower perception threshold settings where tingling is barely felt. Alternate electric field shapes could be used to the described monopolar field. For example, dorsal horn fields that use strips of cathodes (or anodes) along the lead array may be used since they are designed to minimize dorsal column recruitment.

Figure 18:
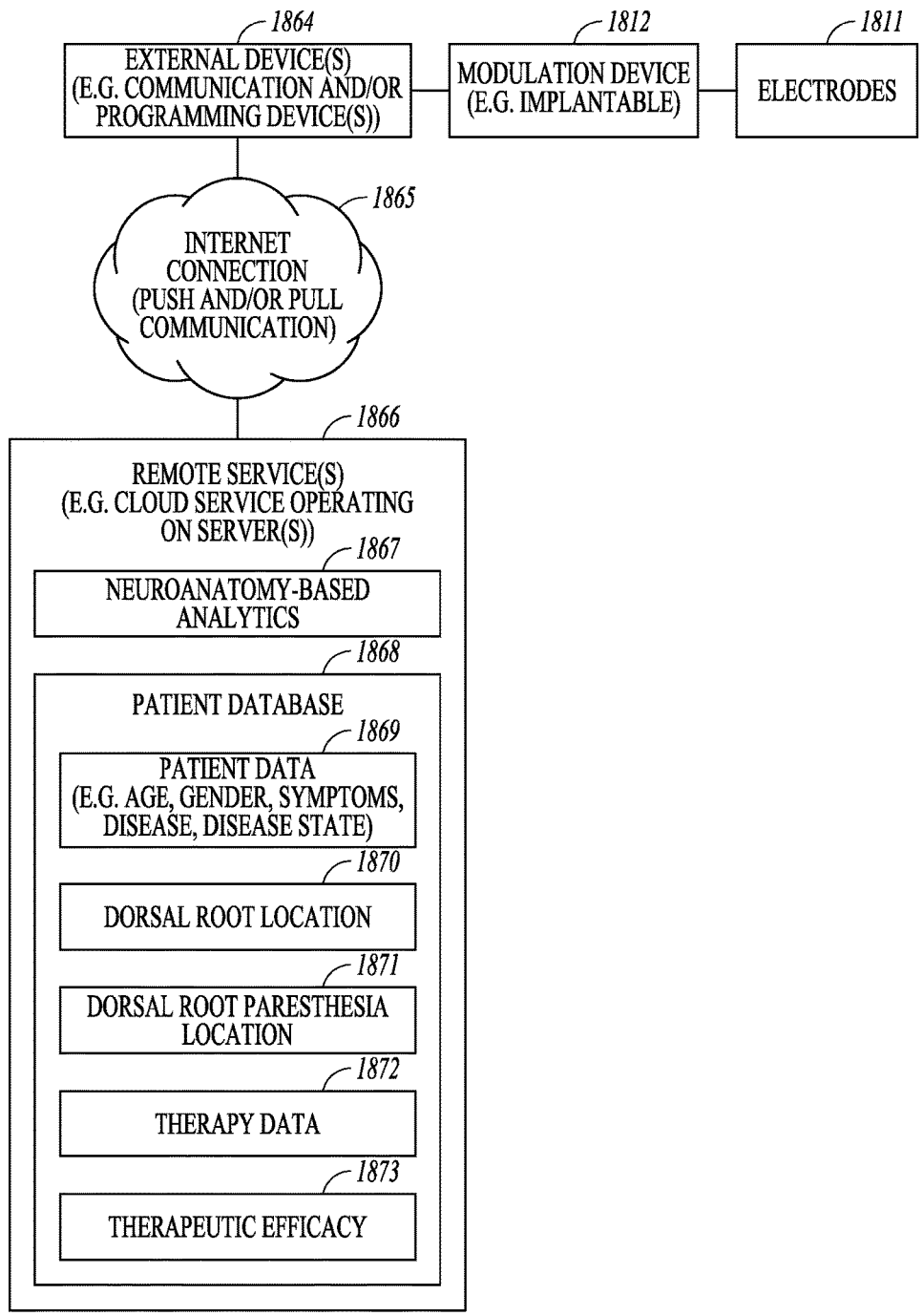
FIG. 18 illustrates an example of a system with data analytics.

FIG. 18 illustrates an example of a system with data analytics. The illustrated system may include electrodes 1811, a modulation device 1812 such as an implantable neural modulation device, and external device(s) 1864. External devices may include programming capabilities for programming the modulation device 1812, and may include communication capabilities for communicating with remote service(s) 1866 through an Internet connection 1865 or other long-range network. The external device(s) may be networked together through a wired or wireless network. The external device may, for example, connect to the Internet through a cellular network similar to a smart phone. The communication and programming capabilities may be in the same device or in separate devices.

The remote service(s) 1866 may be one or more cloud services operating on one or more remote server(s). The remote service(s) may be configured with application(s) to provide neuroanatomy-based analytics 1867 and a patient database 1868 configured to compile data for a plurality of patients. The data may include patient-specific data 1869 such as data selected from age, gender, symptoms, disease, disease state, etc. The data may also include the dorsal root location 1870, the dorsal root paresthesia location 1871, the therapy data 1872, and the therapy efficacy 1873. This is a non-exhaustive listing of some examples of data. The data may also include, by way of example and not limitation, lead size and location.

Various embodiments may include a GUI that is configured for use by a user, such as a patient or a clinician or other caregiver, to receive information for a given patient but can also aggregate data across patients at a specific clinic or across multiple clinics. The system may be configured to push new data from a CP into the cloud and retrieve updated data from the cloud, thus allowing the system to access a large data set.

This large data set may be used to assist the implantation of the electrodes within a new patient, as the data may be analyzed to identify a nerve root location that corresponds to an effective location to deliver SCS therapy for a particular disease. Also, the specific information for the new patient can be included in the data set to provide additional data points for analysis to better identify effective locations for modulation in future patients.

FIG. 19 illustrates a body image 1974 along with an image of bony anatomy 1975 associated with spinal column. The images may be displayed on a GUI of an external device such as a programmer, for example. The false color region 1976 on the body image may be used to identify a pain location. The system is configured to determine where there is a highest chance of delivering effective modulation for targeted pain, and the bony anatomy may identify a desired position of the electrode arrangement, where it has been determined that there is a high or highest chance to treat the pain identified on the body location. This may be represented as false color over the bony anatomy.

FIG. 20 illustrates a plot of therapy success against a dorsal root location. The plot may be on a GUI of an external device such as a programmer. This plot may be an output of the neuroanatomy-based analytics to identify a most likely dorsal root location for success for a specific SCS therapy to treat a specific condition. Histograms for many patients may be used to determine the best neuroanatomical levels (e.g. T7/T8) to treat a specific condition. Pain paresthesia overlap may not be the best manner to predict the effectiveness of electrode placement. Rather, it may be better to look at neuroanatomical levels that predict a better response. The histogram is provided as an example of a way to display analytical data. This analytical data may be displayed in other forms.

FIG. 21 illustrates an image that may be illustrated an on a GUI of an external device such as a programmer, for example. The image may be displayed by the system after a pain pattern has been entered. For example, the pain pattern may be entered on a body image displayed on the GUI. Also, by way of example, an entered pain pattern may be low back and foot pain. The image may illustrate a chance of success for a SCS therapy to treat the low back and foot pain. The image illustrates a representation of neuroanatomy in the span, and provides three separate indicators of success. The first indicator of success 2177 spans the T8-T10 dorsal roots. The second indicator of success 2178 indicates a greater chance of success than the first indicator of success 2177, and indicates that that it is expected to be more successful if the electrode arrangement is positioned to stimulate between the T8 and T9 root. The third indicator of success 2179 indicates a greater chance of success than the second indicator of success 2178 and indicates that it is expected to be more successful if the therapy electrode arrangement is positioned to stimulate just above the T9 root.

Figure 22A:
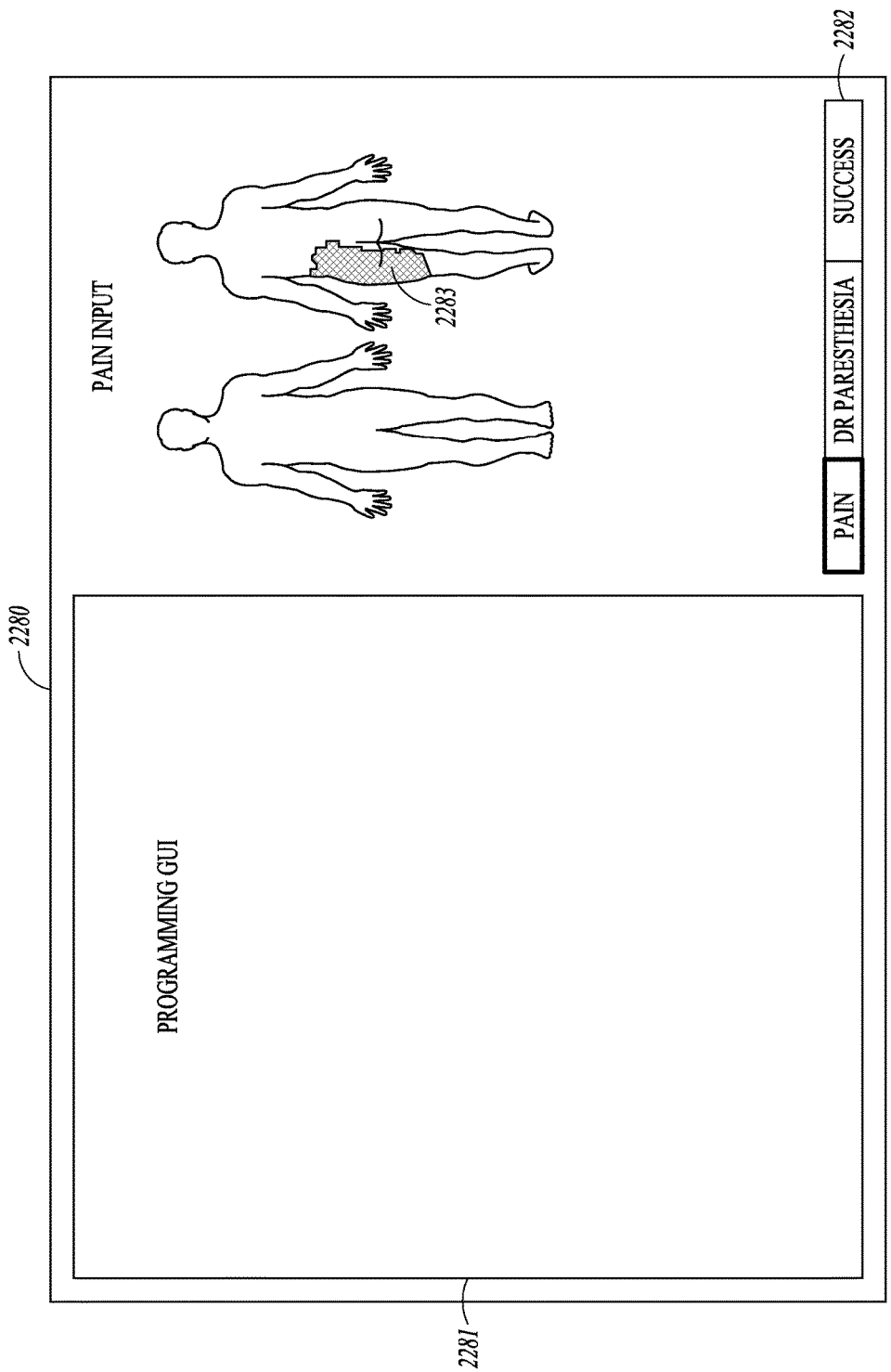
FIGS. 22A-22C illustrate an example of a graphical user interface of an external device that may be used to program a neural modulation device.
Figure 22B:
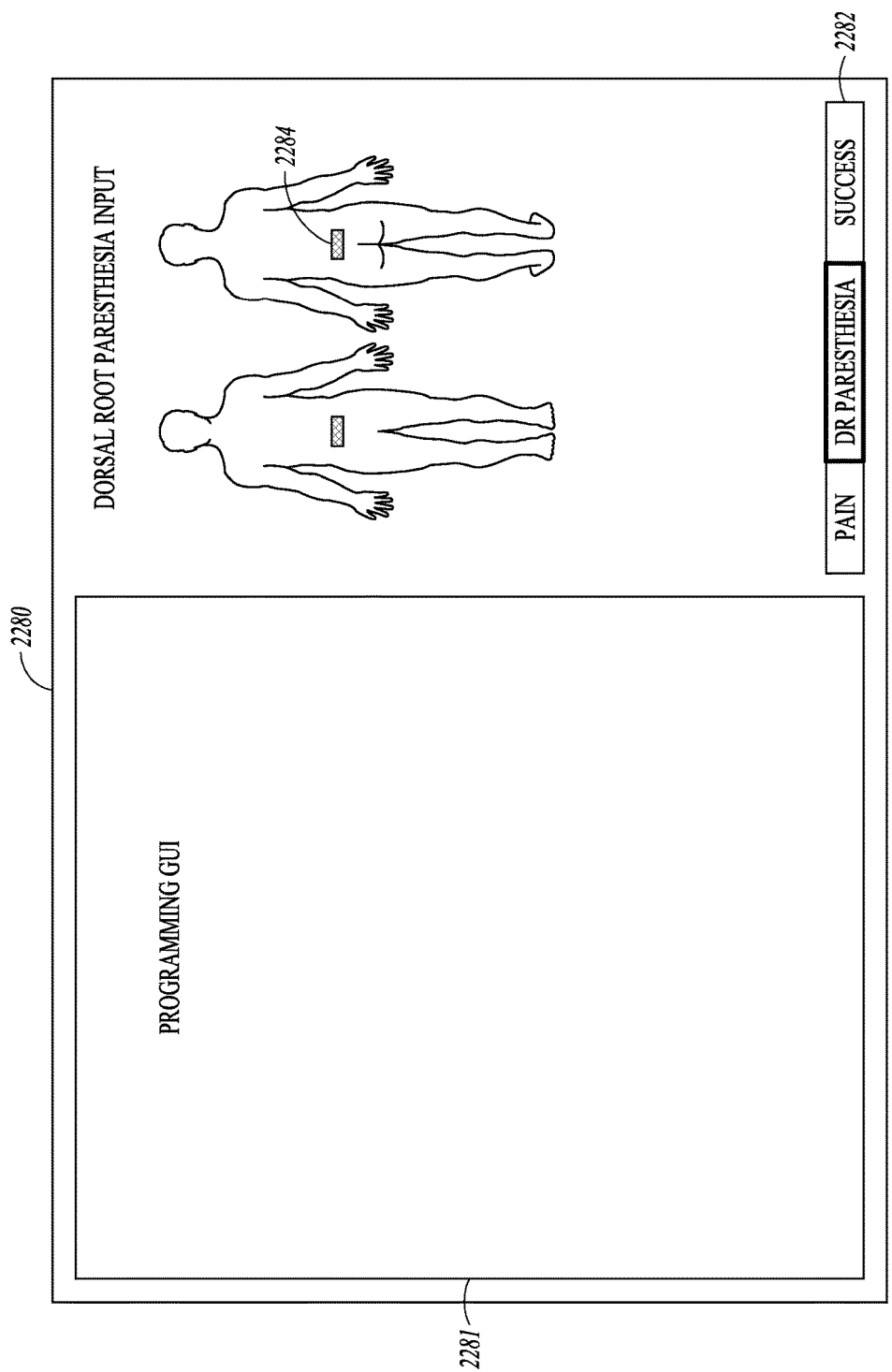
Figure 22C:
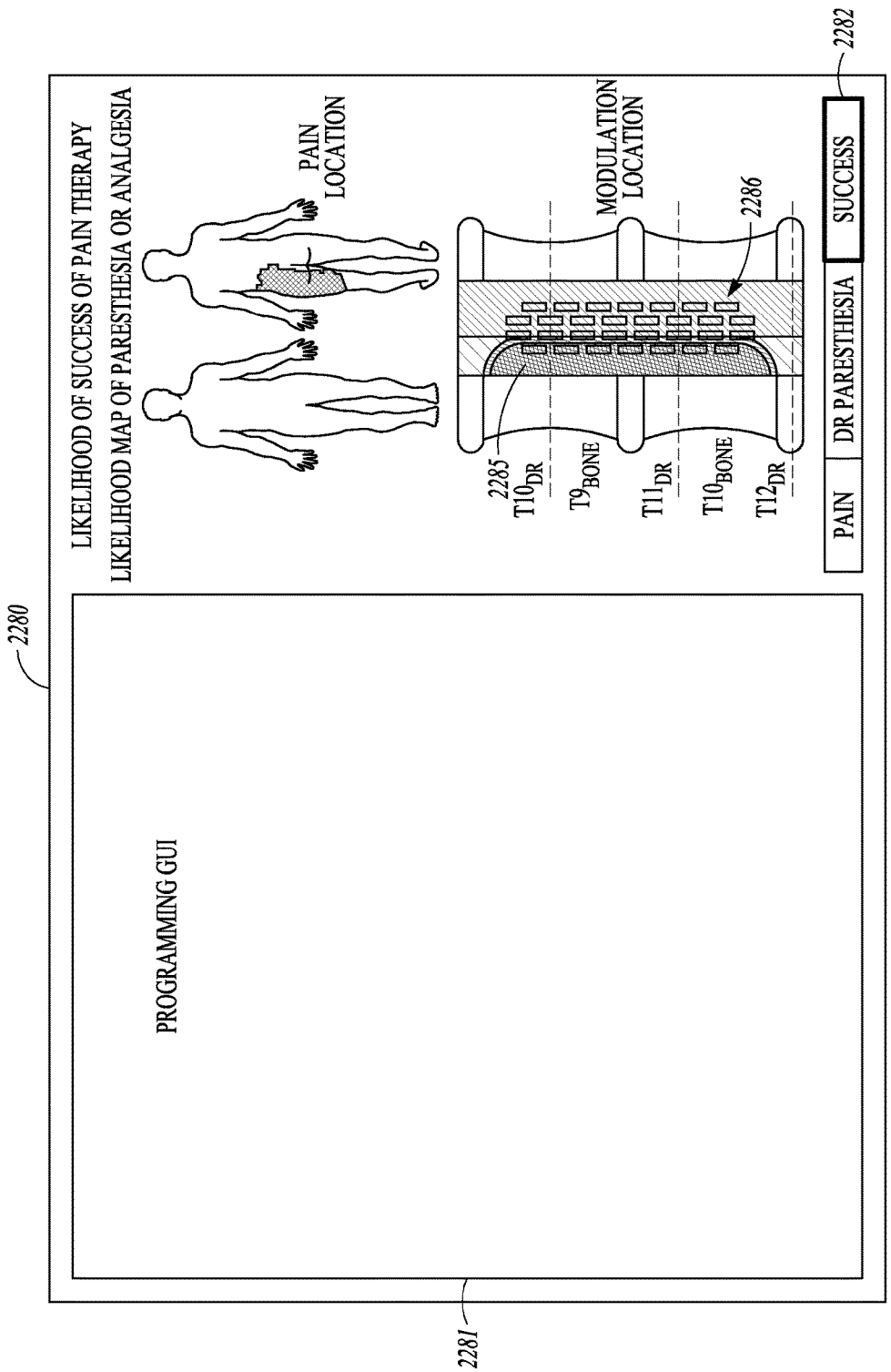

FIGS. 22A-22C illustrate an example of a graphical user interface 2280 of an external device, such as external device 1864 in FIG. 18, that may be used to program a neural modulation device, such as modulation device 1812 in FIG. 18. A portion of the graphical user interface includes a programming graphical user interface 2281 such as may be used to program an electrode configuration (e.g. select active electrodes and determine the fractionalized current for the selected active electrodes). The graphical user interface may also be used to input data into the patient database, such as database 1868 in FIG. 18. By way of examples, tabs 2282 or other navigational tools may be used to provide the different displays. In FIG. 22A, for example, the user (e.g. patient or clinician) may identify the area(s) of pain experienced by the patient. By way of example and not limitation, the system may be configured to allow the patient to draw the areas of the pain on a body image such as is generally illustrated at 2283 or to select different areas by touch those areas on the body image. The graphical user interface may allow the user to enter a mode to perform a placement procedure where supra-perception dorsal root modulation is delivered In FIG. 22B, the user may identify the area(s) of paresthesia experienced by the patient when the supra-perception dorsal root modulation is trolled along the array to modulate different dorsal roots. For example, the system may prompt the user to record on the body image the highest level, dermatomally, that the patient felt tingling during the trolling of the supra-perception dorsal root modulation such as may be generally illustrated at 2284. This patient-specific information for pain and for dorsal root paresthesia may be added to the database 1868 in FIG. 18 to increase the data points and improve the neuroanatomy-based analytics 1867. Similar tabs may be used to provide additional information, such as whether a programmed electrode configuration used to generate a modulate field at a given neuroanatomical location was effective in mapping paresthesia onto the pain for conventional SCS therapy or in mapping areas of analgesia onto the pain for sub-perception modulation.

Regardless of whether the patient information is used to provide additional data points into the database, the system may be configured to provide the clinician with information concerning the likelihood of success of a pain therapy to alleviate the specific area of pain such as is generally illustrated in FIG. 22C. For example, a Success tab may display a representation of the area of pain, along with a representation of the lead location along the spinal cord. False colors, or hatch patterns, or other indicia may be used to identify a likelihood of success (e.g. high, medium or low likelihood of success) if a modulation field is generated near certain neuroanatomical locations (e.g. nerve root locations). This likelihood of success may be determined by the neuroanatomy based analytics 1867 illustrated in FIG. 18. In the example illustrated in FIG. 22C, the highest likelihood of success is if the modulation field is delivered along the left side of the electrode arrangement 2286 as illustrated by the dense cross hatching 2285, and a lower likelihood of success is if the modulation field is delivered at other regions of the electrode arrangement, as illustrated by the less dense cross hatching. The mapping may be displayed with dorsal root information (e.g. $T10_{DR}$, $T11_{DR}$, $T12_{DR}$) and/or with bony anatomy information (e.g., $T9_{BONE}$, $T10_{BONE}$). Some embodiments may note the location of multiple dorsal root levels that were determined electrically. Some embodiments may include a key to help identify how the indicator (e.g. color or hatching or other indicator) corresponds to the likelihood of success. This information may be used to place the leads during implantation, or to program the modulation field after the leads have been implanted.

The above detailed description is intended to be illustrative, and not restrictive. The scope of the disclosure should, therefore, be determined with references to the appended claims, along with the full scope of equivalents to which such claims are entitled.

What is claimed is:

1. A method for placing an electrode arrangement for use to deliver a therapeutic modulation field to a therapeutic modulation target, comprising:
   inserting an electrode arrangement into an epidural space and moving the electrode arrangement within the epidural space; and
   monitoring a position of the electrode arrangement with respect to a supra-perception dorsal root target to position the electrode arrangement in a desired position within the epidural space to deliver the therapeutic modulation field to the therapeutic modulation target, the supra-perception dorsal root target being different from the therapeutic modulation target, wherein the monitoring includes:
   delivering supra-perception threshold stimulation from the electrode arrangement in the epidural space to dorsal roots;
   receiving patient-perception information for the supra-perception threshold stimulation delivered to the dorsal roots, the patient-perception information indicating that the electrode arrangement is in the desired position when the supra-perception threshold stimulation stimulates the supra-perception dorsal root target; and placing the electrode arrangement in the desired position within the epidural space using the patient-perception information.

2. The method of claim 1, further comprising performing a fitting procedure for the electrode arrangement, after placing the electrode arrangement in the desired position, to identify therapeutic modulation parameters for delivering the therapeutic modulation field from the electrode arrangement in the desired position to the therapeutic neural target.

3. The method of claim 2, further comprising delivering therapeutic neural stimulation to the therapeutic neural target using the therapeutic modulation parameters.

4. A method, comprising:
performing a placement procedure, including:
delivering supra-perception threshold modulation from an electrode arrangement in the epidural space to dorsal roots;
receiving patient-perception information for the supra-perception threshold modulation delivered to the dorsal roots; and
using the patient-perception information to either place the electrode arrangement in a desired position within the epidural space where the supra-perception threshold modulation stimulates a supra-perception dorsal root target or place a supra-perception modulation field to modulate the supra-perception dorsal root target; and
delivering therapeutic neural modulation to a therapeutic modulation target using the electrode arrangement in the desired position within the epidural space or using therapeutic modulation parameters derived from parameters used to place the supra-perception modulation field, the supra-perception dorsal root target being different from the therapeutic modulation target.

5. The method of claim 4, wherein the patient-perception information for the supra-perception threshold modulation includes dorsal root paresthesia.

6. The method of claim 4, wherein receiving patient-perception information includes using a body image on a user interface to receive the patient-perception information.

7. The method of claim 4, wherein the patient-perception information for the supra-perception threshold modulation includes a highest level that patient-perceived tingling is felt.

8. The method of claim 4, wherein the therapeutic neural modulation has a larger pulse width than the supra-perception threshold modulation.

9. The method of claim 4, wherein the therapeutic neural modulation includes bipolar modulation and the supra-perception threshold stimulation includes monopolar modulation.

10. The method of claim 4, wherein the supra-perception threshold modulation includes anodic monopolar modulation.

11. The method of claim 4, wherein the supra-perception threshold modulation includes cathodic monopolar modulation.

12. The method of claim 4, further comprising performing a fitting procedure, after placing the electrode arrangement in the desired position, for the placed electrode arrangement to identify therapeutic modulation parameters for delivering a therapeutic modulation field to the therapeutic neural target using the electrode arrangement.

13. The method of claim 4, further comprising:
collecting and aggregating patient data for a plurality of patients, the patient data including dorsal root location of the electrode arrangement and corresponding paresthesia generated for the dorsal root location of the electrode arrangement, and
co-registering patients to identify a likelihood of paresthesia for a supra-perception therapy or a likelihood of analgesia for a sub-perception therapy at selected dorsal roots.

14. The method of claim 4, further comprising creating an atlas based on neuroanatomy.

15. A system, comprising:
an electrode arrangement configured for implantation in an epidural space;
a neural modulation generator configured to use electrodes in the electrode arrangement to generate modulation fields;
at least one storage configured to store supra-perception threshold dorsal root modulation field parameter data and therapeutic modulation field parameter data, the therapeutic modulation field parameter data being different than the supra-perception threshold dorsal root modulation field parameter data; and
a controller operably connected to the neural modulation generator,
the system being configured to:
deliver a placement modulation field from the electrode arrangement in the epidural space to the dorsal roots using the supra-perception threshold dorsal root modulation field parameter data, and receive patient-perception information, the patient-perception information indicating that the electrode arrangement is in a desired position when the supra-perception threshold stimulation stimulates a supra-perception dorsal root target; and
deliver a therapeutic modulation field from the electrode arrangement placed in the desired position within the epidural space to a therapeutic neural target using the therapeutic modulation field parameter data, the supra-perception dorsal root target being different from the therapeutic modulation target.

16. The system of claim 15, wherein the system includes an implantable device and an external device configured to communicate with the implantable device, the external device configured to program the implantable device with the supra-perception threshold dorsal root modulation field parameter data and the therapeutic modulation field parameter data, the external device including a user interface to receive patient-perception information, the user interface including a graphical user interface with a body image configured to allow a patient to enter the patient-perception information by selecting one or more regions of the body image.

17. The system of claim 15, further comprising a remote service with a database accessible through Internet communication, wherein the service is configured to:
receive patient data from a plurality of patients, the patient data including dorsal root location of the electrode arrangement and corresponding paresthesia generated for the dorsal root location of the electrode arrangement;
perform data analytics on the patient data from the plurality of patients;
co-register patients to identify a likelihood of paresthesia for a supra-perception therapy or a likelihood of analgesia for a sub-perception therapy at a dorsal root location; and
create an atlas based on neuroanatomy.

18. The system of claim 15, wherein the therapeutic modulation field has a larger pulse width than the supra-perception threshold modulation field, and the supra-perception threshold modulation field includes monopolar modulation.

19. The system of claim 15, wherein the controller is configured to perform a fitting procedure for the placed electrode arrangement to identify therapeutic modulation parameters for delivering a therapeutic modulation field from the placed electrode arrangement to a therapeutic neural target.

20. The system of claim 15, wherein the therapeutic modulation parameters for delivering the therapeutic modulation field from the placed electrode arrangement in the desired position within the epidural space to the therapeutic neural target includes:
- therapeutic modulation parameters for delivering sub-perception modulation to a neural target selected from the group consisting of: a dorsal column; a dorsal horn; and a dorsal root; or
- therapeutic modulation parameters for delivering a modulation field to a dorsal horn; or
- therapeutic modulation parameters for delivering a modulation field to a dorsal column.

* * * * *